(12) United States Patent
Organ et al.

(10) Patent No.: US 10,583,432 B2
(45) Date of Patent: Mar. 10, 2020

(54) NON-DISRUPTIVE SAMPLER FOR FLUID PROCESSING APPARATUS

(71) Applicants: Michael Organ, Ottawa (CA); Debasis Mallik, Newmarket (CA); Jee Seong Kwak, North York (CA)

(72) Inventors: Michael Organ, Ottawa (CA); Debasis Mallik, Newmarket (CA); Jee Seong Kwak, North York (CA)

( * ) Notice: Subject to any disclaimer, the term of this patent is extended or adjusted under 35 U.S.C. 154(b) by 113 days.

(21) Appl. No.: 15/441,665

(22) Filed: Feb. 24, 2017

(65) Prior Publication Data

US 2017/0248502 A1 Aug. 31, 2017

Related U.S. Application Data

(60) Provisional application No. 62/389,480, filed on Feb. 29, 2016.

(51) Int. Cl.
| | | |
|---|---|---|
| *B01L 3/00* | (2006.01) | |
| *B01L 3/02* | (2006.01) | |
| *G01N 1/10* | (2006.01) | |
| *G01N 35/10* | (2006.01) | |
| *G01N 1/40* | (2006.01) | |

(52) U.S. Cl.
CPC ..... *B01L 3/0293* (2013.01); *B01L 2300/0681* (2013.01); *G01N 2001/4088* (2013.01)

(58) Field of Classification Search
CPC ........ B01L 3/0293; B01L 3/0283; B01L 3/00; G01N 1/2035; G01N 1/20; G01N 1/10; G01N 35/1097; G01N 35/1095; G01N 35/10
USPC ....................................................... 436/177
See application file for complete search history.

(56) References Cited

U.S. PATENT DOCUMENTS

| | | | | |
|---|---|---|---|---|
| 4,577,492 A | * | 3/1986 | Holba | G01N 30/40 210/198.2 |
| 5,389,244 A | * | 2/1995 | Cranston | B01D 29/01 210/106 |
| 8,759,753 B1 | * | 6/2014 | Di Bussolo | B01D 15/325 210/198.2 |
| 2014/0299542 A1 | * | 10/2014 | Song | G01N 30/32 210/635 |

* cited by examiner

*Primary Examiner* — Christine T Mui

(57) ABSTRACT

A sampling module of a fluid processing apparatus includes at least one multi-configuration device connected to a filtration module. The invention relates to an area of non-disruptive sampling from any flow stream including the ones containing solids. The fluid processing apparatus remains in fluid communication with a sample processing module in all configurations of the sampling module and the parameters deemed critical for a chemical process remain unaffected during the sampling event. The entire event is controlled from a computer and the results are collected to make decisions on analytical and process controls.

11 Claims, 39 Drawing Sheets

NON-DISRUPTIVE SAMPLER FOR FLUID PROCESSING APPARATUS

CROSS REFERENCE TO RELATED APPLICATION

This application claims the benefit of 35 USC 119 based on the priority of U.S. Provisional Patent Application 62/389,480 filed on Feb. 29, 2016, this application being incorporated herein by reference.

FIELD

The disclosure relates to a non-disruptive sampler for a fluid processing apparatus. The fluid processing apparatus comprises a lumen, which is populated with one or more reagents. A chemical or physical transformation may take place inside the lumen when appropriate measures are taken. More specifically, the disclosure relates to the inline sampling that can be applied for monitoring the state of matter inside the lumen (the reactor state), to methods and devices for extracting at least a portion of the reactor output and analyzing, and for recording the state of reactor output to implement automations for the intelligent control of the processes. The disclosure is especially useful for applications in which the impact of the sampling event on the reactor state is intended to be minimal and the conservation of process parameters is critical. The disclosure is also applicable when the reactor output that is not necessarily homogeneous in nature, meaning that it is capable of handling homogeneous solutions and those containing solids. The said sampler is designed to handle heterogeneous reactor outputs without any interruption of the fluid processing apparatus or the sampler itself.

BACKGROUND

U.S. Pat. No. 5,602,348 (Takakarhu and Nyfors) purports to disclose a method and an equipment for taking a sample from a slurry. The slurry flow was set at a sufficiently high rate in order to avoid immobilization of particulates on the filter face. A pressure gradient was used to extract the sample from the slurry. Regeneration of the filter membrane to its original state was not addressed.

U.S. Pat. No. 4,501,161 (Endo et al.) purports to disclose an autosampler for sampling from a suspension. According to their claim, two filtering tubes, which are connected to a sampling cell, are immersed in a test solution during sampling. A circulatory pump is used to circulate fluid through the filter membranes and a portion of the test solution enters into the filtering tubes. The filtered solution is sampled from the sampling cell and the residual test solution is returned to the suspension. The residual test solution cannot be analysed. The filtering tubes are immersed in a fluid container and are not suitable for sampling from a flow operation. The sampling mechanism leads to a build-up of residue in the slurried suspension overtime and is not suited for continuous operation.

US Pat. Appl. US 2010/0224012 A1 (Modic et al.) purports to disclose a fluid sample delivery system for filtering solid particles from a liquid sample. The filter membrane comprises three layers of membrane of varying porosity. A displacement plunger with a needle is used to draw samples from a vial or a set of vials on a carousel. A controller, which is capable of monitoring the needle drive slippage, is programmed to detect obstruction and adjust filtering speed to minimize obstructions in the filter membrane. The disclosure does not have a mechanism to restore the filter membrane in its original state for sustainable continuous operation.

U.S. Pat. No. 5,389,244 (Cranston) purports to disclose an enclosed filtration device for hazardous sampling. A circulatory pump was used to receive heterogeneous fluid onto a filter membrane and a set of valves was used to open and close the filtrate line in order to complete the filtration process. The unit required the replacement or the cleaning of the filter membrane between runs. The bottom dish, which traps solids, has to be removed after each filtration. The operation of the device is not suitable for sampling from a continuous stream.

SUMMARY

The following summary is intended to introduce the reader to various aspects of the applicant's teaching, but not to define any invention.

The term 'non-disruptive' used in this summary is intended to define an event of isolating at least a portion of a process fluid without significantly altering any of the process parameters that are deemed critical for the conservation of a process state. The term 'process state' is defined as any quantifiable outcome of a process (e.g., output yield or output purity). The term 'significantly' used in this summary is intended to define a limit of tolerance in the values of the process parameters within which the process state is not impacted.

According to one aspect, a non-disruptive sampling module of a fluid processing apparatus comprises device(s) (e.g. valves, chips, switches) capable of receiving at least one fluid stream from a reactor module of the fluid processing apparatus and diverting at least a portion of the fluid into a fluid holding device (e.g., loops, chips, pipes) mounted on a fluid diverting device. The sampling module maintains fluid communication with a sample processing module of the fluid processing apparatus in all configurations of the fluid diverting device and does not experience significant alteration of any of its process parameters.

In some embodiments, the sampling module is connected to a flow reactor. A flow reactor is a part of the reactor module and is equipped with a mechanism to transport at least one stream of fluid into the flow reactor and dispense at least one stream of treated material to the sample processing module. The sampling module maintains fluid communication with the sample processing module in all configurations and does not require the flow inside the flow reactor to be interrupted during sampling.

In alternate embodiments, the sampling module is connected to a reactor that is not equipped with a mechanism to transport fluid to the sampling module. In those embodiments, additional mechanisms are used to transport the fluid from the reactor module to the sampling module. In alternate embodiments, process pressure is harnessed to move fluid into the sampling module from the reactor module. In another alternate embodiment, negative pressure downstream of the sampling module is used to draw fluid from the reactor module to the sampling module.

In some embodiments, the sampling module is equipped with a filtration module mounted on the fluid diverting device. The filtration module is situated upstream of the fluid holding device and downstream of the reactor module. The filtration module includes an inline filter.

In some embodiments, the inline filter includes a barrier (e.g., a filter membrane) capable trapping solids from the fluid stream based on the porosity of the membrane. The term 'barrier' is used in this summary to encompass flowpaths that trap solids and allow only fluids to permeate through.

In some examples, the barrier allows fluid to move in the forward or the reverse direction based on the pressure gradient across the barrier.

In some embodiments, the fluid diverting device is a multi-port valve.

In alternate embodiments, the filtration module is in fluid communication with a fluid moving device, which is capable of moving a second stream of fluid through the barrier. Also in this configuration, the fluid holding device is in fluid communication with a second fluid moving device, which is capable of transporting the fluid isolated in the fluid holding device to the sample delivery module.

In some embodiments, the sampling module of the fluid processing apparatus is equipped with a second fluid diverting device capable of introducing fluidic additive(s). The device is referred to as the standardization device in this summary for referencing purposes. The device is responsible for delivering any fluidic additives. In these embodiments, the second fluid moving device, which is responsible for moving fluid from the fluid holding device of the sampling valve to the sample delivery module is located upstream of the standardization device.

In some embodiments, the standardization device is a multi-port valve. The valve is equipped with two additional fluid holding devices (a second and a third) and two additional fluid moving devices (a third and a fourth).

In some embodiments, the sampling module of the fluid processing apparatus is located upstream of a sample delivery module.

In some embodiments, the sample delivery module is capable of establishing a fluid communication with a sample analysis module.

In some embodiments, the sampling device is in fluid communication with an additional fluid diverting device (the third) located between the first fluid moving device and the sampling device. The third fluid diverting device is capable of altering the direction of flow of fluid through the filtration module.

In some embodiments, the first fluid diverting device is a multi-port, multi-position valve.

In some embodiments, the multi-port, multi-position valve comprises two separate parts. The part of the valve, which connects peripheral modules and devices (e.g., the reactor module, the sample processing module, sample delivery module, the fluid moving devices, the fluid holding devices, and the filtration module) to the valve is stationary and referred to as the 'stator'. The connection points where the flowpaths from the peripheral modules meet the valve stator are termed as 'ports' in this summary. On the other hand, the part that hosts configurable flowpaths (e.g., channels) to establish fluid communications between any two ports is configurable and referred to as the 'rotor'.

In some embodiments, the rotor is moved so the valve can adopt a configuration.

In some embodiments, the movement of the configurable part of the valve is termed rotation.

In some embodiments, the rotor of the valve is appropriately configured to divert the fluid from the reactor module to the filtration module. The filtered fluid then flows into the fluid holding device. This configuration is defined as a 'load' configuration. In a load configuration, the reactor module is in fluid communication with the sample processing module via the filtration module and the fluid holding device.

In alternate embodiments, the rotor of the valve is appropriately configured to establish fluid communication between the reactor module and the sample processing module bypassing the filtration module. In this configuration, the filtration module is in fluid communication with the first fluid moving device, which is capable of moving a second stream of fluid through the filtration module. Also in this configuration, the fluid holding device is in fluid communication with the second fluid moving device, which is capable of transporting the fluid isolated in the fluid holding device to the sample delivery module. This configuration is termed as an 'inject' configuration.

In some examples, the load and the inject configurations are asynchronus. The term 'asynchronus' implies that the valve can not adopt both configurations at the same time.

In some embodiments, all modules and devices of the fluid processing apparatus are actuated from a controller.

In some embodiments, the controller is a part of a computer.

In some embodiments, the first fluid diverting device is a 'sampling valve' and the second fluid diverting device is a 'standardization valve'.

According to another aspect, a method for sampling fluids comprises a) preparing the sampling module to receive at least one fluid stream from the reactor module; b) configuring the sampling valve to move to a load configuration; c) flowing the fluid stream from the reactor module into the filtration module; d) allowing the filtered fluid to flow into the fluid holding device of the sampling valve for a period of time; e) configuring the sampling valve to move to an inject configuration; f) configuring the first fluid moving device, which is in fluid communication with the filtration module, to move fluid through the filtration module; and g) configuring the second fluid moving device, which is in fluid communication with the fluid holding device and the sample delivery module, to move fluid in the fluid holding device to the sample delivery module.

In some examples, the method further comprises step g1) configuring the standardization valve to move to the load configuration to introduce additional fluidic additive(s) in the fluid holding devices of the standardization valve; step g2) configuring a fluid moving device to flow the fluidic additives into the fluid holding devices of the standardization valve; step g3) configurating the standardization valve to move back to the inject configuration after a period of time.

In some embodiments, the stator of the sampling valve hosts ports which are distributed in one or more concentric rings (circles or channels).

In some embodiments, the sampling valve is a multi-port and multi-ring valve. The configurable portion of the device is capable of setting the device in a 'load' or 'inject' configuration based on the electronic signals received from the controller.

In some embodiments, the standardization valve is an integral part of the stator of the sampling valve and the functions of the standardization valve are executed from the actuation of the sampling valve itself.

According to another aspect, the method for sampling fluids using the multi-port, multi-ring valve comprises a) preparing the sampling module to receive at least one fluid stream from the reactor module; b) configuring the sampling valve to move to a load configuration; c) flowing the fluid stream from the reactor module into the filtration module; d) allowing the filtered fluid to flow into the fluid holding device of the sampling valve for a period of time; e) flowing the fluidic additive streams to the fluid holding devices; f)

configuring the sampling valve to move to an inject configuration; g) configuring the first fluid moving device, which is in fluid communication with the filtration module, to move fluid through the filtration module; and h) configuring the second fluid moving device, which is in fluid communication with all fluid holding devices and the sample delivery module, to move fluid in the fluid holding devices to the sample delivery module.

In some embodiments, the sampling valve is a two-configuration (two-position) valve.

In alternate embodiments, the sampling valve is a multi-configuration (multi-position) valve. In those examples, configuring a valve means rotating the multi-configuration valve to more than two positions asynchronously.

In some positions, the valve establishes a fluid communication between the reactor module and the sample processing module via the filtration module and the fluid holding device. These positions are examples of 'load' positions.

In alternate positions, the valve establishes a fluid communication between the reactor module and the sample processing module bypassing the filtration module and the fluid holding device. In any of these alternate positions, the second fluid moving device, which is in fluid communication with the fluid holding device, moves fluid from the fluid holding device to the sample delivery module. These positions are examples of 'inject' positions.

In some embodiments, the sampling valve is a ten-port, ten-position, two-ring valve. In these embodiments, there are five configurable flowpaths on the rotor of the sampling valve. There are five asynchronus 'load' and five asynchronus 'inject' positions. Two consecutive 'load' positions are 72° apart. Two consecutive 'inject' positions are 72° apart. A 'load' position and a consecutive 'inject' position are 36° apart.

According to another aspect, a method for sampling fluids using the multi-position valve comprises a) preparing the sampling module to receive at least one fluid stream from the reactor module; b) configuring the sampling valve to move to one of the available load configurations; c) flowing the fluid stream from the reactor module into the filtration module; d) allowing the filtered fluid to flow into the fluid holding device of the sampling valve for a period of time; e) configuring the sampling valve to move to one of the available inject configurations; f) configuring the first fluid moving device, which is in fluid communication with the filtration module, to move fluid through the filtration module; and g) configuring the second fluid moving device, which is in fluid communication with the fluid holding device and the sample delivery module, to move fluid in the fluid holding device to the sample delivery module.

In some methods, steps b), c), d) and f) are repeated using available 'load' positions of the sampling valve.

In some methods, the 'load' positions are chosen in such a way so that the configurable flowpath, which was receiving fluid from the reactor module in one 'load' position, is placed in a new 'load' position so the first fluid moving device can move a secondary fluid stream through the configurable flowpath in the new 'load' position.

In some examples, the secondary fluid stream is used for cleaning purposes.

In some methods, the method further comprises step h) configuring the sampling valve to rotate to new 'inject' position. The steps of moving the valve to different 'inject' positions continues until a signal is sent from the controller to move the valve to one of the five 'load' positions.

In some methods, the 'inject' positions are chosen in such a way so that the configurable flowpath, which was receiving fluid from the reactor module in one 'inject' position, is placed at a new 'inject' position so the first fluid moving device can move a secondary fluid stream through the configurable flowpath in the new 'inject' position.

In some examples, the secondary fluid stream is used for cleaning purposes.

In some methods, the selection of an 'inject' position after a 'load' position is done in such a way so the configurable flowpath, which was receiving fluid from the reactor module in the last 'load' position, is placed in an 'inject' position in which the first fluid moving device can move a secondary fluid stream through the configurable flowpath.

In some examples, the secondary fluid stream is used for cleaning purposes.

In some methods, the selection of a 'load' position after an 'inject' position is done in such a way so the configurable flowpath, which was receiving fluid from the reactor module in the last 'inject' position, is placed in a 'load' position in which the first fluid moving device can move a secondary fluid stream through the configurable flowpath.

In some examples, the secondary fluid stream is used for cleaning purposes.

In some examples, the selection of positions (load or inject) is done in such a way so the direction of flow through the configurable flowpaths is altered.

In some methods, any of the method steps are concurrent.

According to another aspect, a method comprises altering flow parameters (e.g., flow-rate, pressure, pulse-rate) of the fluid moving devices based on the results obtained from the sample analysis module.

In some examples, the method comprises altering flow parameters of all modules of the fluid processing apparatus based on the results contained from the sample analysis module.

In some examples, the method for sampling fluids includes analyzing results obtained from the sample analysis module of the fluid processing apparatus and configuring any device of any module based on reported value(s).

According to another aspect, in some embodiments, the filtration module is a configurable device equipped with a set of inline filters; the filtration module is in fluid communication to a reactor module; the reactor module is in fluid communication with a sample processing module via at least one of the multiple inline filters.

In some embodiments, the filtration module adopts at least two configurations; in the first configuration, fluid from the reactor module moves through one of the multiple inline filters and the filtered fluid moves toward the sample processing module; in the second configuration, fluid from the reactor module moves through the second inline filter and the filtered fluid moves toward the sample processing module.

In some embodiments, during the first configuration, a fluid moving device moves a secondary fluid stream through the second inline filter; in the second configuration, the fluid moving device moves the secondary fluid stream through the first inline filter.

In some embodiments, the filtration module is in a fluid communication with the sample processing module via a fluid diverting device, which is located downstream of the filtration module. In these embodiments, the reactor module is always in fluid communication with the sample processing module, but via the filtration module and the fluid diverting device. The fluid diverting device is configurable and is a part of the sampling module.

In some embodiments, the fluid diverting device adopts at least two asynchronus configurations; in the first configuration, the reactor module establishes a fluid communication with the sample processing module via a fluid holding device mounted on the fluid diverting device. This configuration is referred to as a 'load' configuration; in the second configuration, the reactor module establishes a fluid communication with the sample processing module bypassing the fluid holding device of the fluid diverting device. This configuration is referred to as an 'inject' configuration; In the inject configuration, a second fluid moving device establishes a fluid communication with the fluid holding device and a sample delivery module and moves the fluid in the fluid holding device to the sample delivery module.

In some examples, the sample delivery module moves fluid to a sample analysis module.

According to another aspect, a method for using the filtration module equipped with the set of inline filters comprises a) moving fluid from the reactor module through the first inline filter of the filtration module; b) configuring the first fluid moving device to move a secondary fluid stream through the second inline filter of the filtration module; c) allowing the filtration module to remain in this configuration for a period of time; d) configuring the filtration module to move to the second configuration so fluid from the reactor module moves through the second inline filter of the filtration module and the secondary fluid stream from the fluid moving device moves through the first inline filter.

In some examples, the method further comprises e) configuring the sampling valve to move to the 'load' configuration; f) configuring the sampling valve to move back to the 'inject' configuration after a period of time; g) configuring the second fluid moving device to move fluid in the fluid holding device of the sampling valve to the sample delivery module.

In some examples, the method further comprises h) configuring the sample delivery module to move at least a portion of the fluid to the sample analysis module.

In some embodiments, the configurable device of the filtration module is a multi-port, multi-configuration (multi-position) filtration valve.

In some embodiments, the filtration valve is a ten-port, ten-position filtration valve.

In some embodiments, the ten-port, ten-position filtration valve is capable of rotating by 36° at a time to adopt ten asynchronus positions (from the first to the tenth); the reactor module is in fluid communication with one of the inline filters in any of the five odd-numbered positions; the reactor module is in fluid communication with the second inline filter in any of the five even-numbered positions.

In some examples, the method to operate on the multi-position filtration module further comprises actuating the filtration module in such a way so the configurable flowpath, which was receiving fluid from the reactor module in one configuration, moves to a new configuration where the flowpath can establish a fluid communication with the first fluid moving device; the first fluid moving device moves a secondary fluid stream through the configurable flowpath in the new configuration.

In some examples, the secondary fluid stream is for cleaning purposes.

In some embodiments, a multiple number of filtration modules are in fluid communication with the reactor module. In some embodiments, the fluid communications among the multiple filtration modules are in series. In alternate embodiments, the fluid communications among the filtration modules are in parallel.

BRIEF DESCRIPTION OF THE DRAWINGS

The drawings included herewith are for illustrating various examples of articles, methods, modules and devices of the present specification and are not intended to limit the scope of what is taught in any way. In certain figures where individual device configurations are deemed useful, figure labels are followed by subscripts indicating the configuration of the individual devices for clarity (e.g., the fluid communications between ports). In the drawings.

Figure 1:
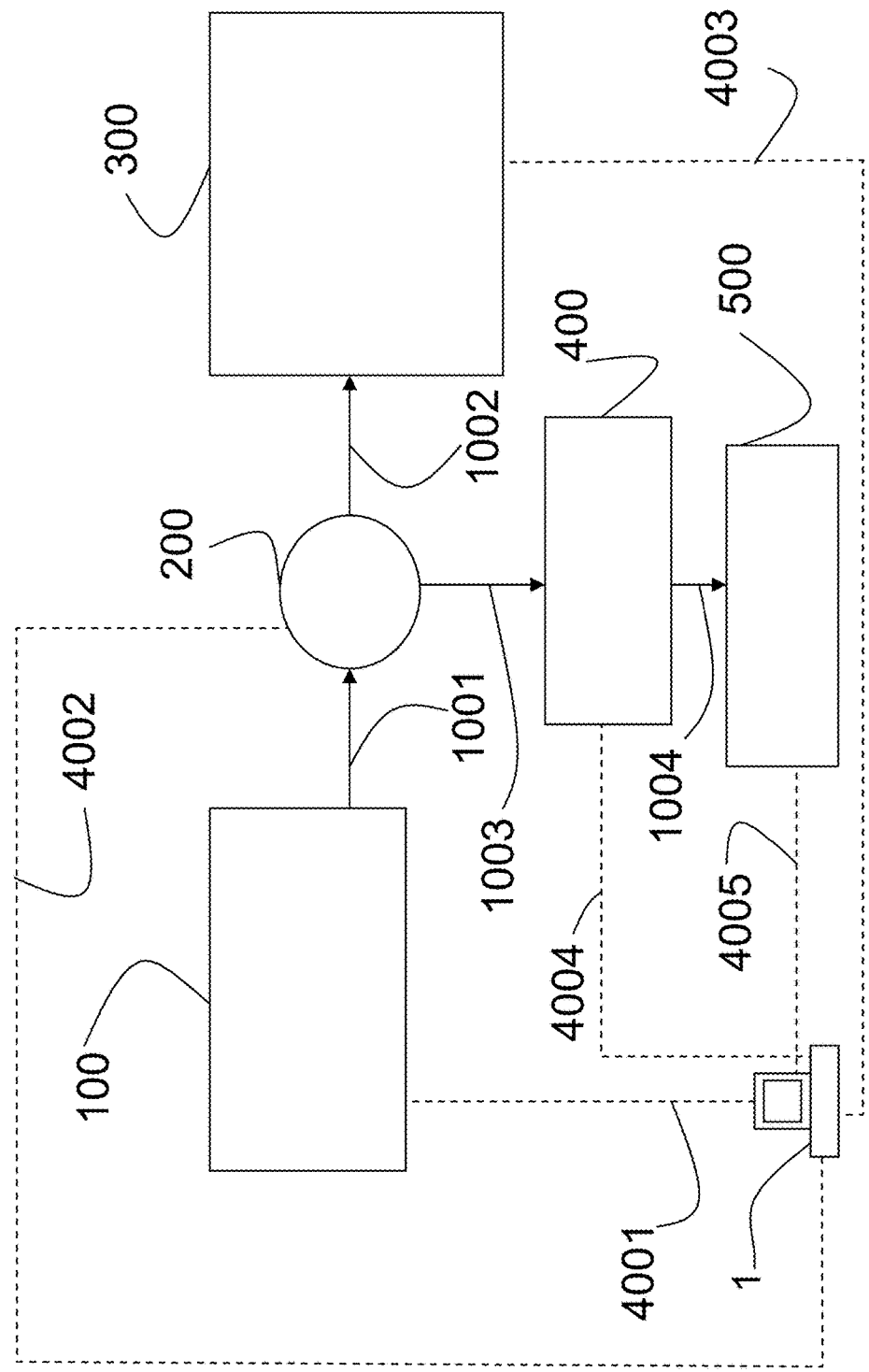
FIG. 1 is a flow diagram of an example of the fluid processing apparatus; the apparatus includes a reactor module, a sampling module, a sample processing module, a sample delivery module, a sample analysis module, and a controller.
Figure 12:
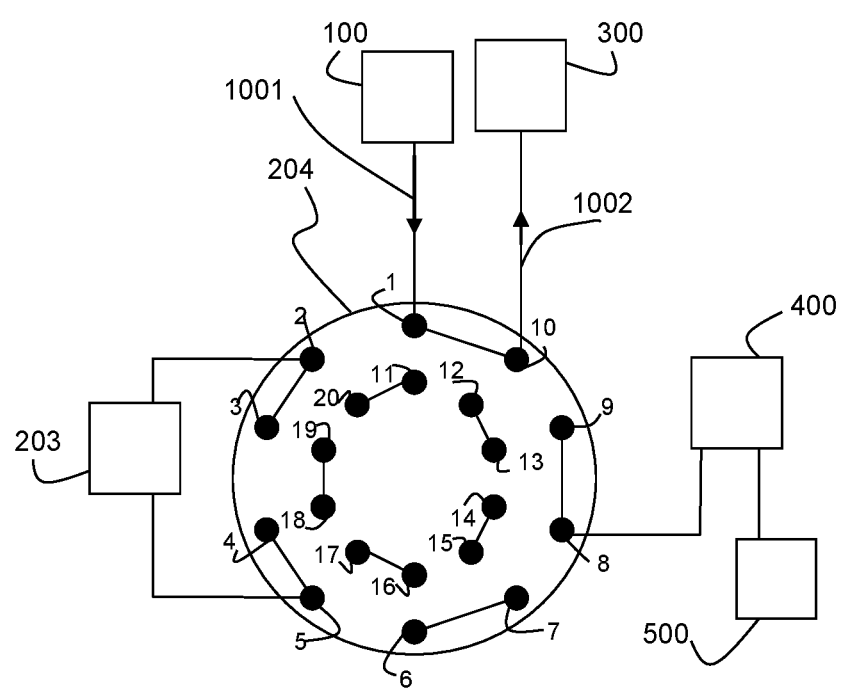

FIG. $4_{1-2/11-12}$ is a flow diagram of the sampling module of the fluid processing apparatus of FIG. 1, showing an embodiment of the individual device configurations; the sampling device is in a configuration (inject) suitable to filter the fluid from the reactor module. The filtered fluid is collected in a fluid holding device mounted on the sampling device. The standardization device is in a configuration (load) in which the fluid holding devices mounted on the standardization device can be filled with fluidic additives. The subscript on the figure label (e.g., $_{1-2/11-12}$) indicates the configurations of the sampling and the standardization devices respectively. The first two digits in the subscript (in this example, $_{1-2}$) suggest that the sampling device is in a configuration such that the ports 1 and 2 are in fluid communication. It is imperative that when the ports 1 and 2 are in fluid communication, the port 3 and 4, 5 and 6, 7 and 8, 9 and 10 are also in fluid communications. Similarly, the last two digits in the subscript (in this example, $_{11-12}$) suggest that the standardization device is in a configuration such that the ports 11 and 12 are in fluid communication. It is imperative that when the ports 11 and 12 are in fluid communication, the port 13 and 14, 15 and 16, 17 and 18, 19 and 20 are also in fluid communications;

FIG. $5_{1-10/11-20}$ is a flow diagram of the sampling module of the fluid processing apparatus of FIG. 1, showing an embodiment of the individual device configurations; the sampling and the standardization devices are in a configuration (inject) suitable to transport fluids from all fluid holding devices to the sample delivery module. The subscript on the figure label (e.g., $_{1-10/11-20}$) indicates the configuration of the sampling device and the standardization device respectively; The first two digits in the subscript (in this example, $_{1-10}$) suggest that the sampling device is in a configuration such that the ports 1 and 10 are in fluid communication. It is imperative that when the ports 1 and 10 are in fluid communication, the port 2 and 3, 4 and 5, 6 and 7, 8 and 9 are also in fluid communications. Similarly, the last two digits in the subscript (in this example, $_{11\text{-}20}$) suggest that the standardization device is in a configuration such that the ports 11 and 20 are in fluid communication. It is imperative that when the ports 11 and 20 are in fluid communication, the port 12 and 13, 14 and 15, 16 and 17, 18 and 19 are also in fluid communications;

FIG. $6_{1\text{-}10/11\text{-}12}$ is a flow diagram of the sampling module of the fluid processing apparatus of FIG. 1, showing an embodiment of the individual device configurations; the sampling and the standardization devices are in a configuration to transport fluid only from the fluid holding device of the sampling to the sample delivery module. In this example, fluidic additives from the standardization device are not transported to the sample delivery module. This is an example of analysis when the analysis may not require any fluidic additive from the standardization device. The subscript on the figure label (e.g., $_{1\text{-}10/11\text{-}12}$) indicates the configurations of the sampling and the standardization devices respectively;

FIG. $7_{1\text{-}2/11\text{-}20}$ is a flow diagram of the sampling module of the fluid processing apparatus of FIG. 1, showing an example of the individual device configurations; the sampling and the standardization devices are in a configuration so that the fluid from the reactor module is filtered and collected in the fluid holding device of the sampling device; the standardization device is not in fluid communication with the fluid stream from the reactor module. In this configuration, in some examples, fluid paths of the standardization device are cleaned and the waste stream is diverted to waste via the sample delivery module. The subscript on the figure label (e.g., $_{1\text{-}2/11\text{-}20}$) indicates the configurations of the sampling and the standardization devices respectively;

FIG. $8_{1\text{-}2/11\text{-}12}$ is a flow diagram of the sampling module of the fluid processing apparatus of FIG. 1, showing an embodiment of the sampling device equipped with an inline filter; the sampling device is in a configuration (load) suitable to filter the fluid from the reactor module and then collect the filtered fluid in the fluid holding device. The direction of flow in the inline filter is shown in the figure. The subscript on the figure label (e.g., $_{1\text{-}2/11\text{-}12}$) indicates the configurations of the sampling and the standardization devices respectively;

FIG. $9_{1\text{-}10/11\text{-}12}$ is a flow diagram of the sampling module of the fluid processing apparatus of FIG. 1, showing an embodiment of the sampling equipped with an inline filter; the sampling device is in a configuration (inject) so the inline filter is in fluid communication with a fluid moving device and the fluid in the fluid holding device is in fluid communication with a second fluid moving device capable of transporting the fluid from the fluid holding device (the analyte) to the sample analysis module via the sample delivery module. The direction of flow in the inline filter is shown in the figure. The subscript on the figure label (e.g., $_{1\text{-}10/11\text{-}12}$) indicates the configurations of the sampling and the standardization devices respectively;

FIG. $10_{1\text{-}10/11\text{-}12/21\text{-}22}$ is a flow diagram of the sampling module of the fluid processing apparatus of FIG. 1, showing an embodiment of the individual device configurations; the sampling device is equipped with an inline filter; the sampling device is in an inject configuration; a new fluid diverting device (the third); is located upstream of the first fluid moving device and downstream of the sampling device; the configuration of the third fluid diverting device is such that the direction of flow of fluid through the inline filter is opposite to that when the sampling device is in a 'load' configuration. The subscript on the figure label (e.g., $_{1\text{-}10/11\text{-}12/21\text{-}22}$) indicates the configurations of the sampling valve, the standardization valve, and the third fluid diverting device respectively;

FIG. $11_{1\text{-}10/11\text{-}12/21\text{-}24}$ is a flow diagram of the sampling module of the fluid processing apparatus of FIG. 1, showing an embodiment of the individual device configurations; the sampling device is in an inject configuration; the configuration of the third fluid diverting device is such that the direction of flow of fluid through the inline filter is same as that when the sampling device is in a 'load' configuration. The subscript on the figure label (e.g., $_{1\text{-}10/11\text{-}12/21\text{-}24}$) indicates the configurations of the sampling valve, the standardization valve, and the third fluid diverting device respectively;

FIG. 12 is a flow diagram of the sampling module of the fluid processing apparatus of FIG. 1, showing all peripheral fluid handling devices and their connectivities; the sampling module includes a fluid diverting device, which is a multi-port, multi-ring valve; the multi-ring fluid diverting device is capable of functioning as the sampling device as well as the standardization device.

FIG. $13_{1\text{-}2/(11\text{-}12)}$ is a flow diagram of the sampling module of the fluid processing apparatus of FIG. 1, showing an embodiment of the multi-ring fluid diverting device configuration; the fluid diverting device is in a configuration (load) so the fluid from the reactor output is filtered by the filtration module and then collected in the first fluid holding device. Also in this configuration, other fluid holding devices (the second and the third) are in fluid communication with the respective fluid moving devices (the third and the fourth) and capable of receiving fluidic additives. The subscript on the figure label (e.g., $_{1\text{-}2/(11\text{-}12)}$) indicates the configuration of the multi-ring fluid diverting device. The secondary connectivity (shown in parentheses) is indicated for clarity. It is imperative that the connectivities indicated in parentheses are set in accordance with the primary connectivities (e.g., $_{1\text{-}2}$);

FIG. $14_{1\text{-}10/(11\text{-}20)}$ is a flow diagram of the sampling module of the fluid processing apparatus of FIG. 1, showing an embodiment of the multi-ring fluid diverting device configuration; the fluid diverting device is in a configuration (inject) so the fluid from all fluid holding devices is in fluid communication with the sample analysis module via the sample delivery module. The subscript on the figure label (e.g., $_{1\text{-}10/(11\text{-}20)}$) indicates the configuration of the sampling valve. The secondary connectivity (shown in parentheses) is indicated for clarity. It is imperative that the connectivities indicated in parentheses are set in accordance with the primary connectivities (e.g., $_{1\text{-}10}$);

FIG. $15_{21\text{-}22/33\text{-}32/41\text{-}46}$ is a flow diagram of the sampling module of the fluid processing apparatus of FIG. 1, showing an embodiment of the filtration module equipped with two inline filters; the first inline filter is used to remove solids from the fluid coming from the reactor module; the second inline filter is in fluid communication with a fluid moving device. The filtered fluid is collected in a fluid holding device mounted on a fluid diverting device. The first fluid diverting device is a sampling device. A second fluid moving device and a second fluid diverting device are located upstream of the sampling device. The second fluid diverting device is a standardization device. There is an additional fluid diverting device (the third) between the fluid moving device and the filtration module. The purpose of the third fluid diverting device is to change the direction of flow of fluid through the inline filters. The subscript on the figure label (e.g., $_{21\text{-}22/33\text{-}32/41\text{-}46}$) indicates the configurations of the filtration module, the third fluid diverting device, and the sampling device respectively;

FIG. $16_{21\text{-}30/31\text{-}32/41\text{-}46}$ is a flow diagram of the sampling module of the fluid processing apparatus of FIG. 1, showing an embodiment of the filtration module equipped with two inline filters; the sampling device is in a 'load' configuration; the third fluid diverting device is in a second configuration. The subscript on the figure label (e.g., $_{21\text{-}30/31\text{-}32/41\text{-}46}$) indicates the configurations of the filtration module, the third fluid diverting device, and the sampling device respectively;

FIG. $17_{21\text{-}30/31\text{-}32/41\text{-}42}$ is a flow diagram of the sampling module of the fluid processing apparatus of FIG. 1, showing an embodiment of the filtration module equipped with two inline filters; the sampling device is in an 'inject' configuration. The subscript on the figure label (e.g., $_{21\text{-}30/31\text{-}32/41\text{-}42}$) indicates the configurations of the filtration module, the third fluid diverting device, and the sampling device respectively;

FIG. $18_{21\text{-}30/31\text{-}32/41\text{-}42/51\text{-}54}$ and FIG. $19_{21\text{-}30/31\text{-}32/41\text{-}42/51\text{-}52}$ are a flow diagrams of the sampling module of the fluid processing apparatus of FIG. 1, showing an embodiment of the filtration module equipped with two inline filters; In these embodiments, a fourth fluid diverting device, which is responsible for altering the direction of flow through the inline filters, is shown. The subscripts on the figure labels (e.g., $_{21\text{-}30/31\text{-}32/41\text{-}42/51\text{-}54}$ or $_{21\text{-}30/31\text{-}32/41\text{-}42/51\text{-}52}$) indicate the configurations of the filtration module, the third fluid diverting device, the sampling device, and the fourth fluid diverting device respectively;

FIG. $20_{1\text{-}2}$ is a flow diagram of the sampling module of the fluid processing apparatus of FIG. 1; In this embodiment, individual configurable flowpaths on the rotor portion of the sampling device are shown. This is a ten-port, ten-position device. The described configuration is a 'load' configuration.

FIG. $21_{1\text{-}10}$ is a flow diagram of the sampling module of the fluid processing apparatus of FIG. 1; In this embodiment, configurable flowpaths on the rotor portion of the sampling device are shown; In this configuration, one configurable flowpath is filled with the fluid from the reactor module and another flowpath is emptied. The configurable flowpath that is receiving fluid from the reactor module is marked with "back-slashed" lines and the configurable flowpath that is being emptied of the fluid by the first fluid moving device is marked with "dotted" lines. The described configuration is an 'inject' configuration.

FIGS. $22_{1\text{-}2}$, $23_{1\text{-}10}$, $24_{1\text{-}2}$, $25_{1\text{-}10}$, $26_{1\text{-}2}$, $27_{1\text{-}10}$, $28_{1\text{-}2}$, $29_{1\text{-}10}$, $30_{1\text{-}2}$, and $31_{1\text{-}10}$ are flow diagrams of the sampling module of the fluid processing apparatus of FIG. 1, showing embodiments of several 'load' and 'inject' configurations of the multi-position device; the "back-slashed" and the "dotted" lines are used to mark respective configurable flowpaths that are being filled with and emptied of the fluid from the reactor module during a particular configuration.

FIG. $32_{1\text{-}2/(11\text{-}12)}$ is a flow diagram of the sampling module of the fluid processing apparatus of FIG. 1, showing an embodiment of the sampling device in a 'load' configuration; the sampling device is a multi-port, multi-position, and multi-ring valve; configurable flowpaths connecting ports from 1 to 10 are labelled as 20001 to 20005. The flowpaths connecting ports from 11 to 20 are shown, but not labelled; the configurable flowpaths connecting the ports between 11 and 20 may not come in contact with the fluid from the reactor module; the configurable flowpath that is being filled with the fluid from the reactor module is marked with "back-slashed" lines and the configurable flowpath that is being emptied of the fluid by the fluid moving device is marked with "dotted" lines. In this figure, flowpath 20005 is being filled with the fluid from the reactor module and flowpath 20001 is being emptied. The sampling device is in a 'load' configuration.

FIG. $33_{1\text{-}10/(11\text{-}20)}$ is a flow diagram of the sampling module of the fluid processing apparatus of FIG. 1, showing an embodiment of the sampling device in an 'inject' configuration. In this figure, flowpath 20004 is being filled with the fluid from the reactor module and flowpath 20005 is being emptied.

FIGS. $34_{1\text{-}2/(11\text{-}12)}$, and $35_{1\text{-}10/(11\text{-}20)}$ are flow diagrams of the sampling module of the fluid processing apparatus of FIG. 1, showing embodiments of the fluid diverting device in several 'inject' and 'load' configurations; In FIG. $34_{1\text{-}21(11\text{-}12)}$, flowpath 20003 is being filled with the fluid from the reactor module and flowpath 20004 is being emptied. This is a 'load' configuration. In FIG. $35_{1\text{-}10/(11\text{-}20)}$, flowpath 20002 is being filled with the fluid from the reactor module and flowpath 20003 is being emptied. This is an 'inject' configuration.

FIGS. $36_{21\text{-}30/31\text{-}32}$, $37_{21\text{-}22/31\text{-}34}$, $38_{21\text{-}30/31\text{-}32}$, and $39_{21\text{-}22/31\text{-}34}$ are flow diagrams of the sampling module of the fluid processing apparatus of FIG. 1, showing several embodiments of the filtration module in two degenerate configurations; configurable flowpaths connecting ports from 21 to 30 of the filtration module are labelled as 30001 to 30005 in each diagram; the configurable flowpath that is being filled with the fluid from the reactor module is marked with "back-slashed" lines and the configurable flowwpath that is being emptied of the fluid by the fluid moving device is marked with "dotted" lines in each diagram.

SUMMARY OF INVENTION

The sampling module of a fluid processing apparatus according to the subject of invention includes a design and a method to filter fluid in a filtration module and isolate at least a portion of the filtered fluid from the main stream of the fluid processing apparatus in a fluid holding device. At least a portion of the isolated fluid is transported from the fluid holding device to a sample analysis module via a sample delivery module. The entire setup and the method are capable of functioning without any interruption during the operation of the fluid processing apparatus. The filtration module is capable of flushing the barrier in the forward or the reverse direction. The filtration is either done using a single inline filter (one sampling at a time) or from a device equipped with alternating multiple inline filters (continuous sampling). The filtered fluid is transported to the sample analysis module for analysis or to waste. The module is also equipped with a standardization device capable of introducing fluidic additive(s). The sampling and standardization operations are either done from a single device (better synchronicity) or from multiple devices (diverse functionality). The sampling method uses multiple configurations of the fluid diverting devices so the flowpaths responsible for receiving fluid (specifically, the configurable flowpaths on the rotor portion of the fluid diverting device) are cleaned in between their uses. The multi-configuration method (as opposed to the two-configuration (load and inject) method) broadens the scope of sampling to fluids of greater heterogeneity.

DETAILED DESCRIPTION

Various devices or processes will be described below to provide an example of an embodiment of the invention. No embodiment described below limits any claimed invention and any claimed invention may cover methods or devices that differ from those described below. The claimed invention is not limited to devices or methods having all of the features of any one device or method described below or to features common to multiple or all of the devices described below. It is possible that a device or method described below is not an embodiment of any exclusive right granted by issuance of this patent application. Any invention disclosed in a device or method described below and for which an exclusive right is not granted by issuance of this patent application may be the subject matter of another protective instrument, for example, a continuing patent application, and the applicants, inventors or owners do not intend to abandon, disclaim or dedicate to the public any such invention by its disclosure in this document.

Referring to FIG. 1, an embodiment of the fluid processing apparatus is shown. The fluid processing apparatus generally includes a reactor module 100, a sampling module 200, a sample processing module 300, a sample delivery module 400, a sample analysis module 500, and a controller 1.

Referring still to FIG. 1, the controller 1 is connected to the reactor module 100, the sampling module 200, the sample processing module 300, the sample delivery module 400, and the sample analysis module 500 via communication pathways 4001, 4002, 4003, 4004, and 4005 respectively. The communication pathways are used to send signals to the individual modules from the controller 1.

Referring still to FIG. 1, the reactor module 100 is connected to the sampling module 200 via a fluid path 1001. The sampling module 200 is connected to the sample processing module 300 via a fluid path 1002. The sample module 200 is also connected to the sample delivery module 400 via a fluid path 1003. The sample delivery module 400 is connected to the sample analysis module 500 via a fluid path 1004. The sample delivery module 400 is programmable and is capable of diverting fluid to waste or to the sample analysis module 500.

Referring still to FIG. 1, the reactor module 100 is capable of receiving at least one fluid stream and dispensing at least a portion of the fluid stream to the sample processing module 300 via the sampling module 200. The sampling module 200 is capable of diverting at least a portion of the fluid stream to the sample delivery module 400.

Figure 2:
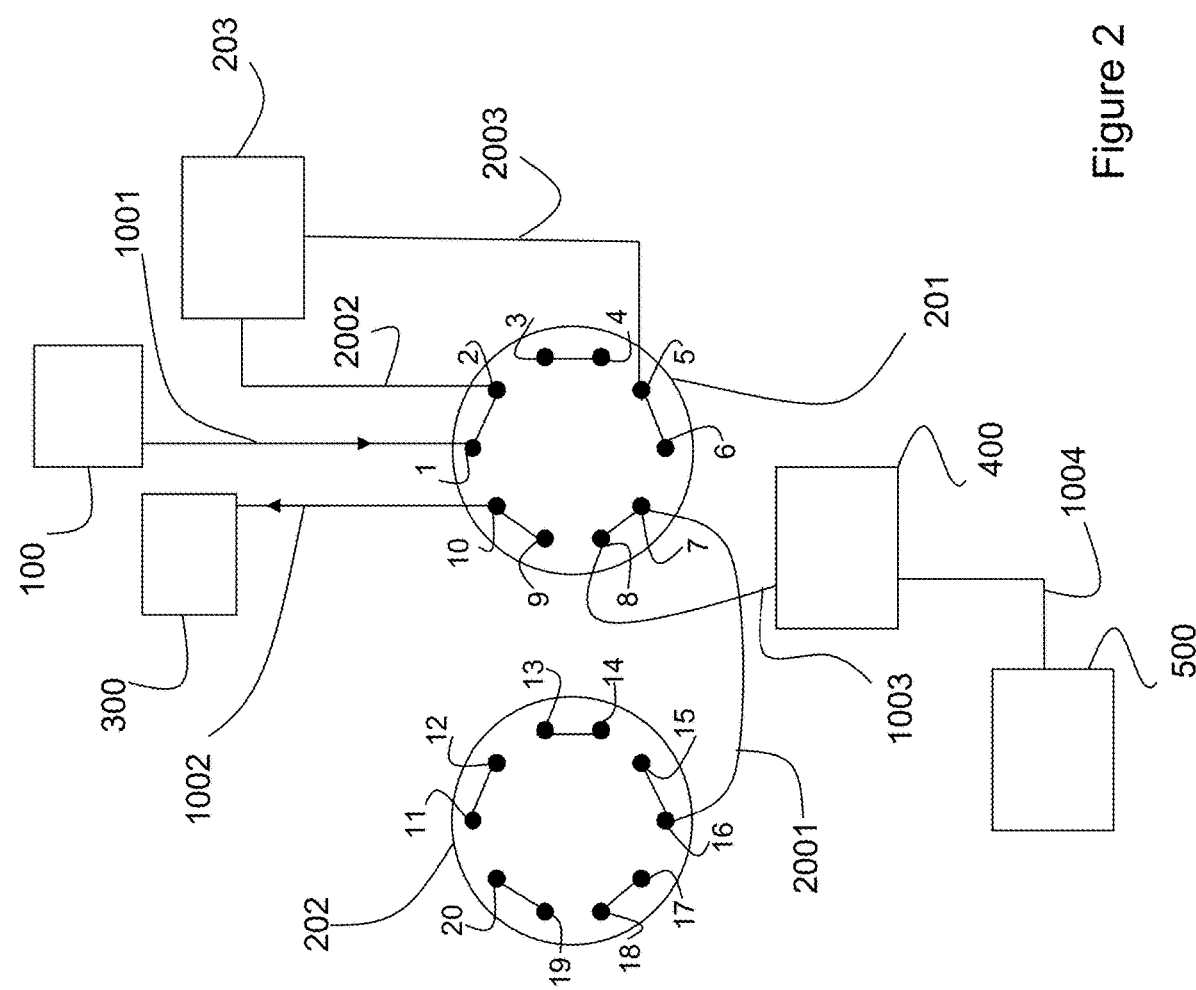
FIG. 2 is a flow diagram of the sampling module of the fluid processing apparatus of FIG. 1. In this embodiment, the sampling module includes a fluid diverting device, which is in fluid communication with a filtration module. A second fluid diverting device, which is capable of introducing fluidic additives to the sampling module, is in fluid communication with the first fluid diverting device. The first fluid diverting device is in fluid communication with the sample processing and sample delivery modules.

Referring to FIG. 2, the sampling module 200 includes a set of multi-port fluid diverting devices (e.g., valves, chips, switches) capable of isolating at least a portion of the fluid from the reactor module 100. In the embodiment shown, a multi-port valve 201 is in fluid communication with the reactor module 100 via the fluid path 1001 (specifically, via port 1) and with the sample processing module 300 via the fluid path 1002 (specifically, via port 10).

Referring still to FIG. 2, the valve 201 is in fluid communication with a second multi-port valve 202 via a fluid path 2001 between port 7 of the valve 201 and port 16 of the valve 202.

Referring still to FIG. 2, in some embodiments, the valve 201 and the valve 202 are ten-port valves.

Referring still to FIG. 2, in some embodiments, the valve 201 and the valve 202 are ten-port, two-position valves. In another embodiment, the valve 201 and the valve 202 are ten-port, multi-position valves.

Referring still to FIG. 2, specifically, the port 8 of the valve 201 is connected to the sample delivery module 400 via the fluid path 1003.

Referring still to FIG. 2, the port 2 and 5 of the valve 201 are connected to a filtration module 203 via fluidic paths 2002 and 2003 respectively.

Referring still to FIG. 2, fluid from the reactor module 100 moves through the filtration module 203 via the fluid path 2002 first and then the filtered fluid enters the fluid path 2003, which is located downstream of the filtration module 203 and upstream of the port 5 of the valve 201. The filtered portion of the fluid, which is held in the fluid path 2003, is referred to as the 'filtrate'. Similarly, the fluid which is held in the fluid path 2002 and contains matter (for example, solids) that is incapable of passing through the filtration module 203. This filterable matter is termed the 'residue'.

Figure 3:
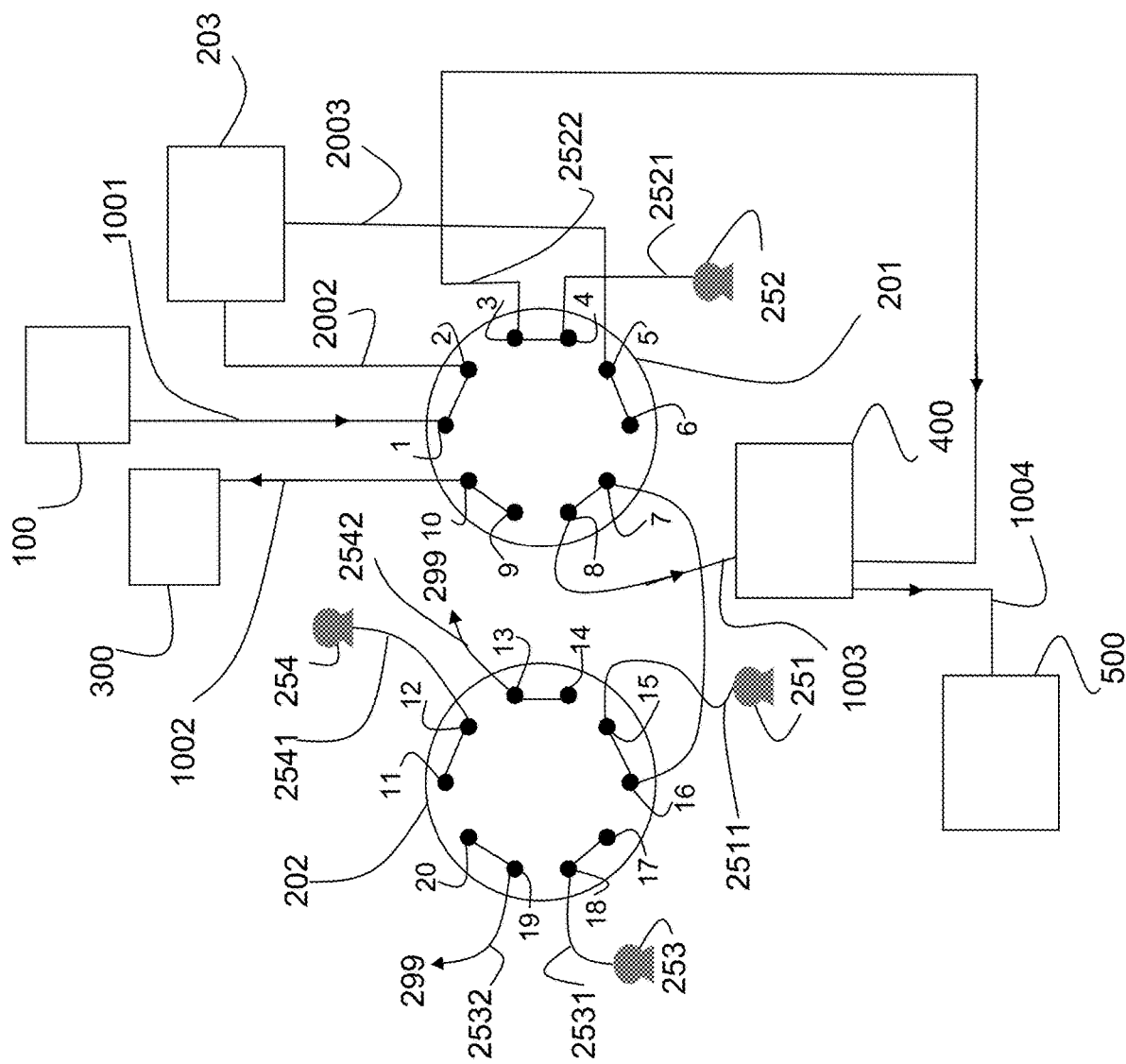
FIG. 3 is a flow diagram of the sampling module of the fluid processing apparatus of FIG. 1, showing some peripheral fluid handling devices and their connectivities. The first fluid diverting device is a sampling device and the second fluid diverting devices is a standardization device.
Figure 4:
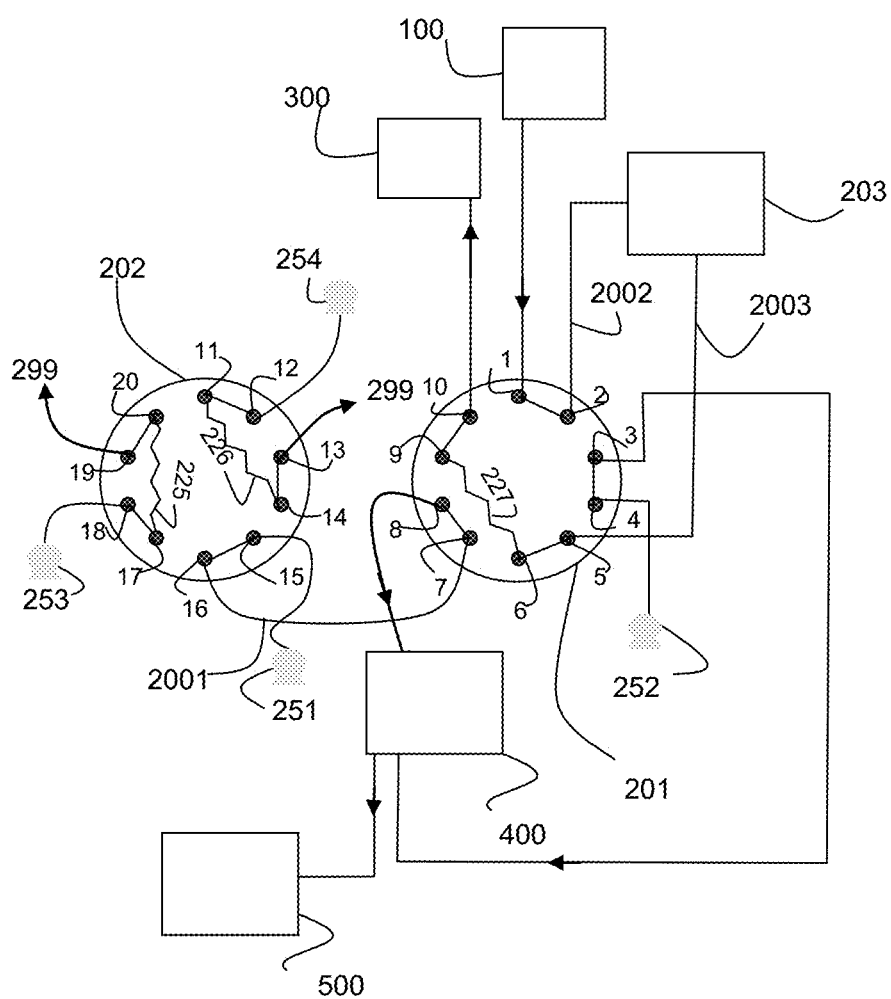
Figure 5:
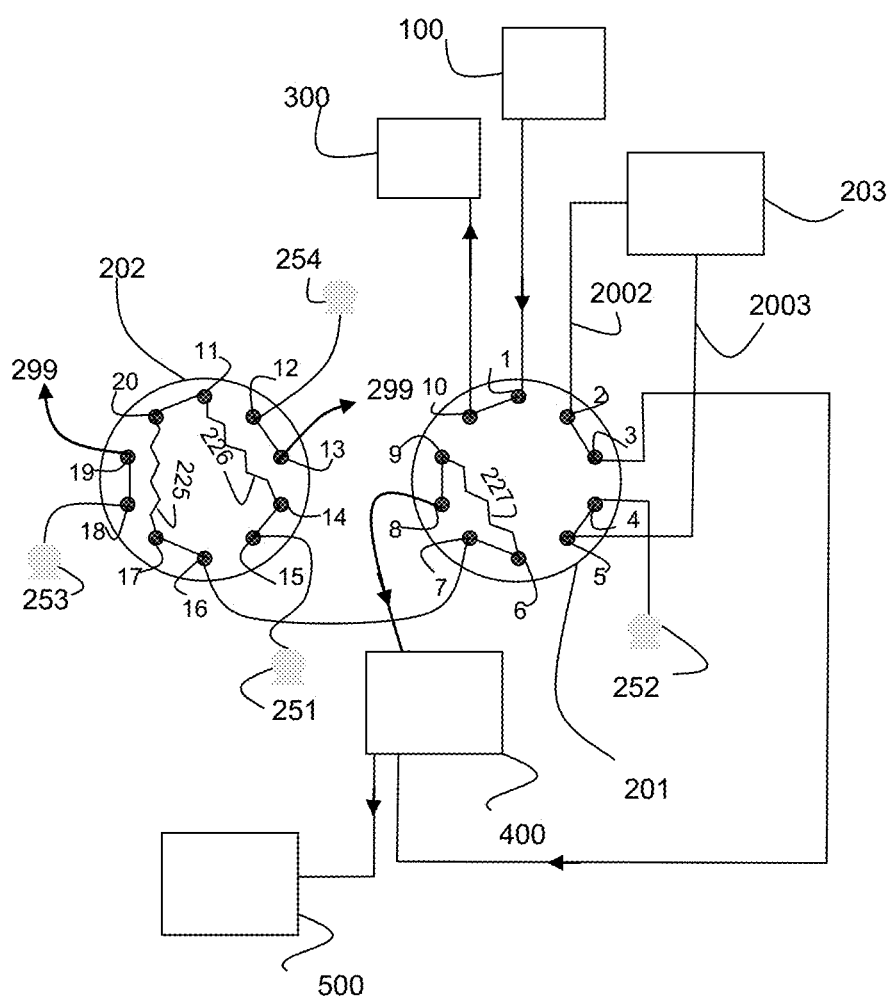
Figure 6:
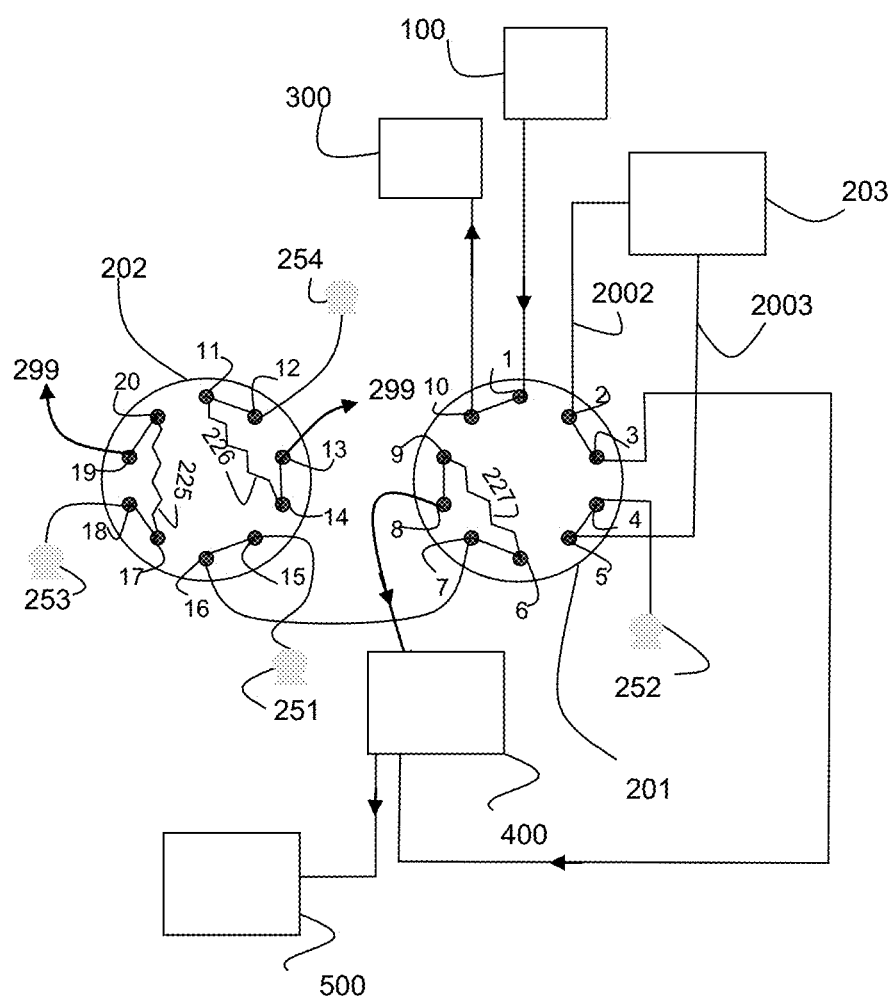
Figure 7:
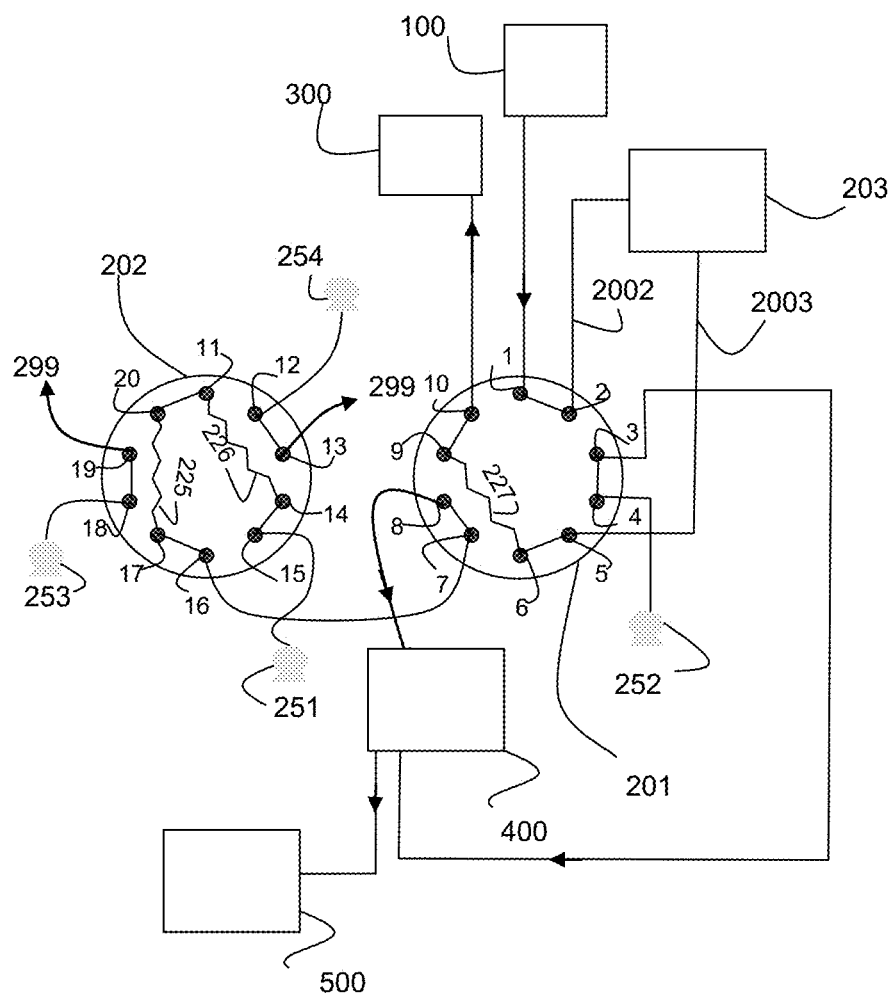
Figure 8:
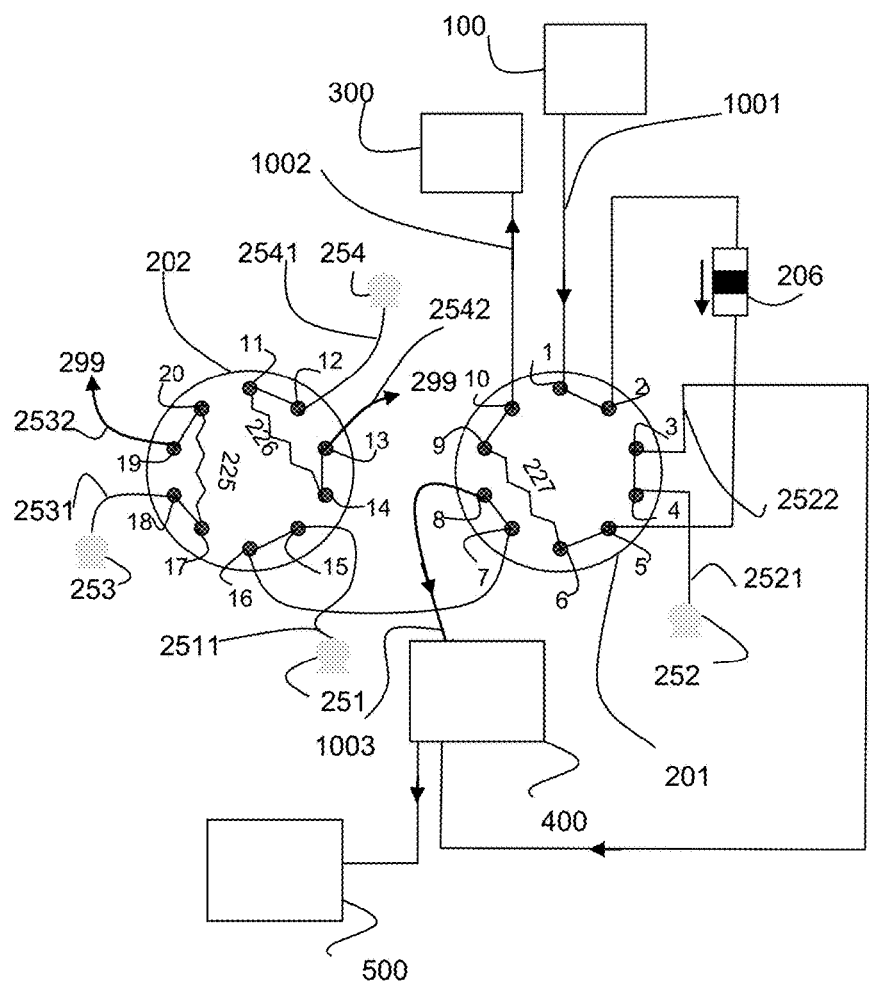
Figure 9:
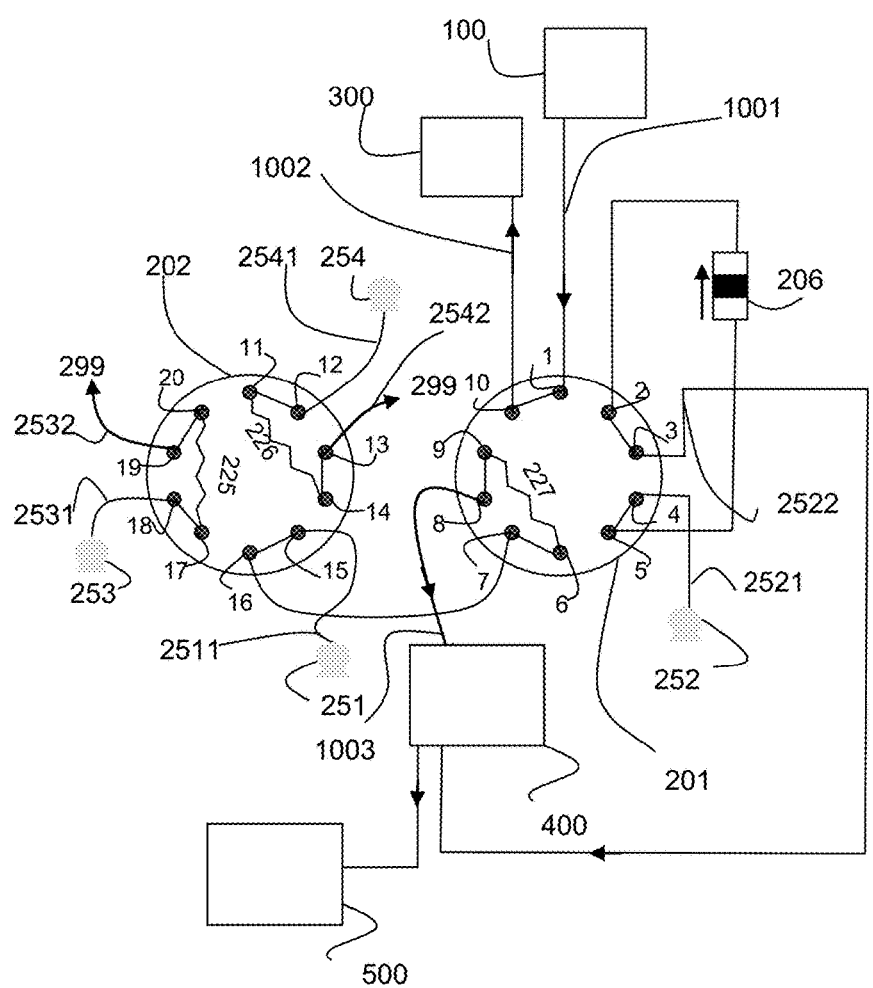
Figure 10:
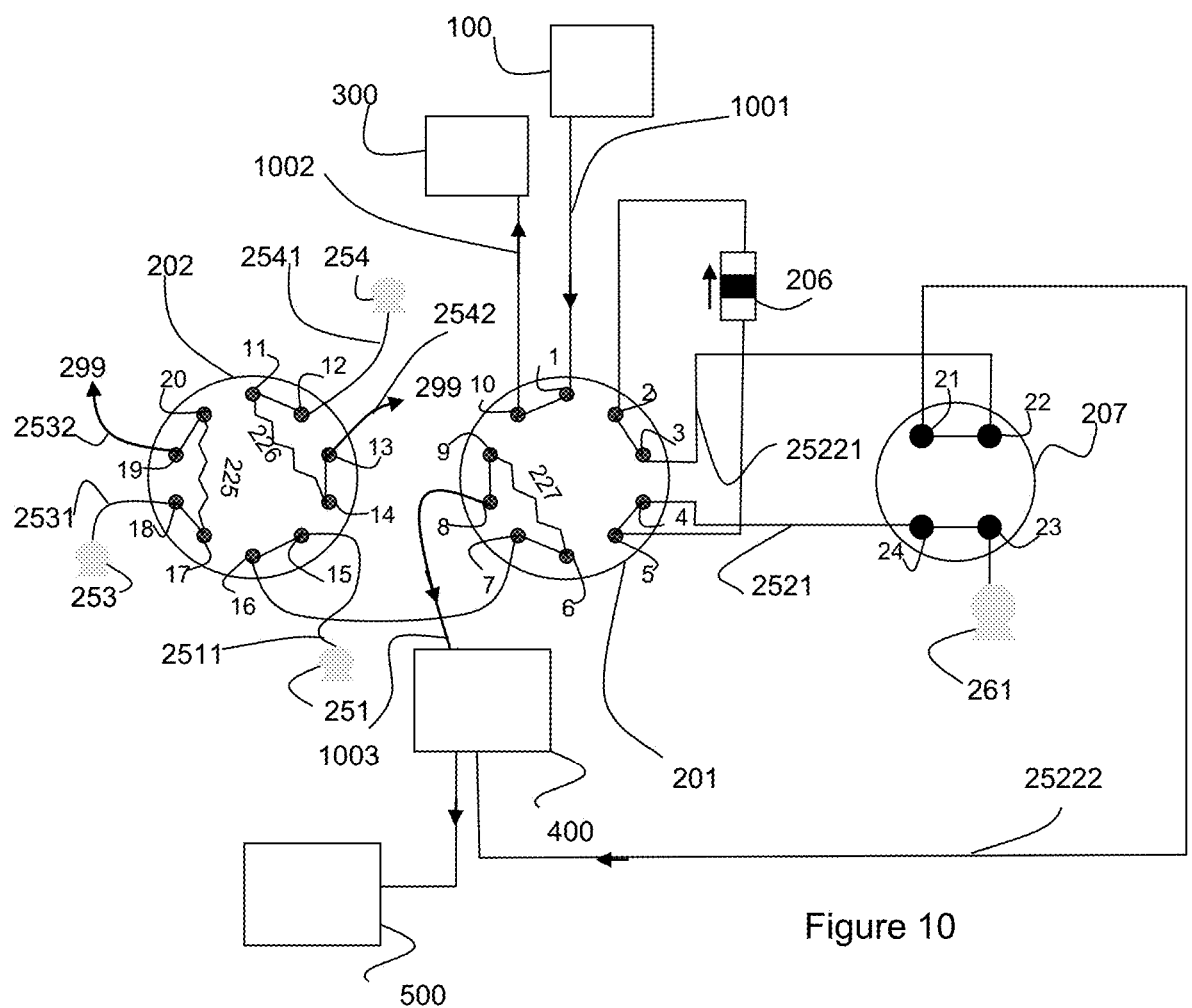
Figure 11:
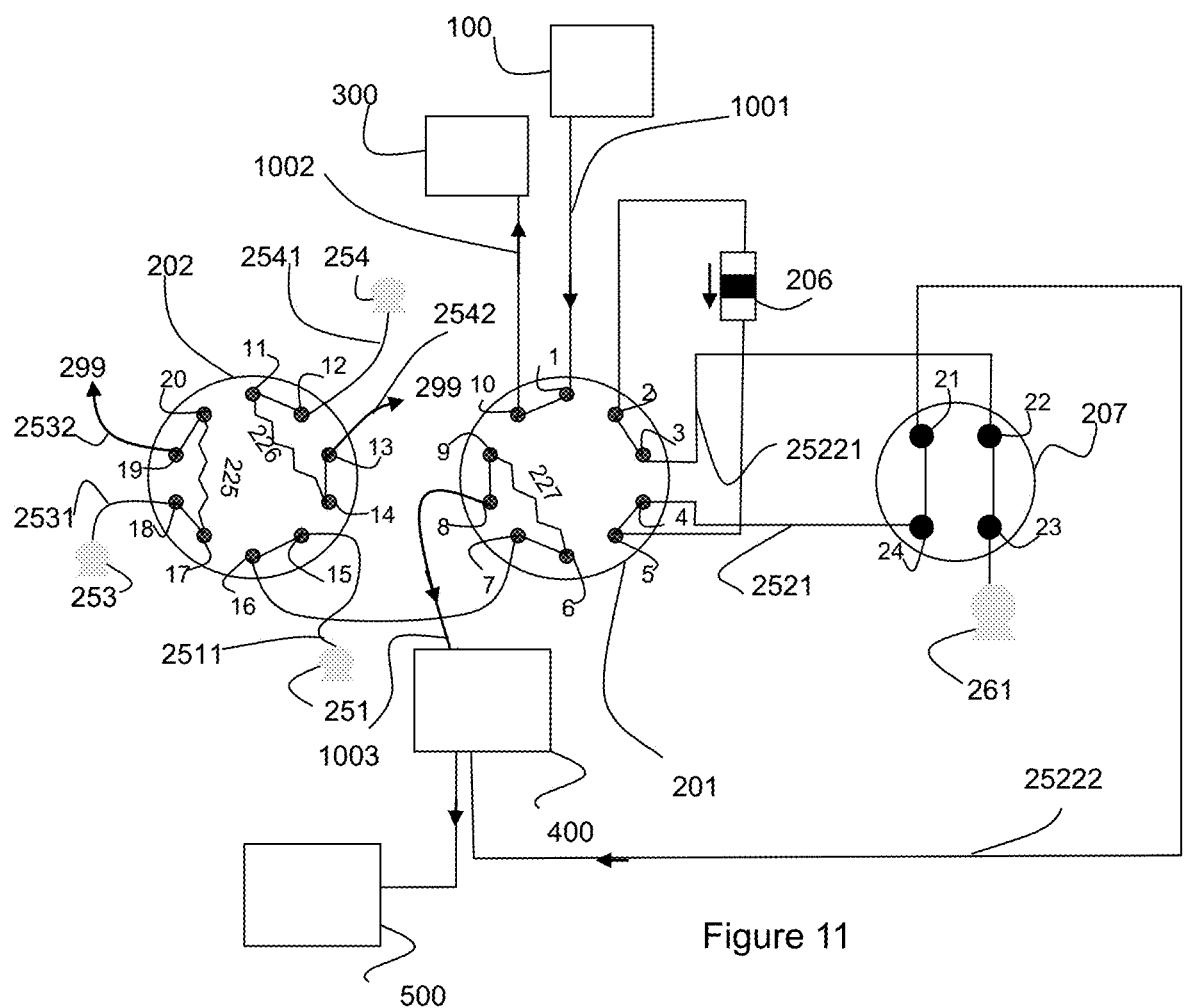

Referring to FIG. 3, a fluid moving device 251 is connected to port 15 of the valve 202 via a fluid path 2511.

Referring still to FIG. 3, a fluid moving device 252 is connected to port 4 of the valve 201 via a fluid path of 2521.

Referring still to FIG. 3, a fluid moving device 253 is connected to port 18 of the valve 202 via a fluid path 2531.

Referring still to FIG. 3, a fluid moving device 254 is connected to port 12 of the valve 202 via a fluid path of 2541.

Referring still to FIG. 3, ports 13 and 19 of the valve 202 are connected to waste 299 via fluid paths 2542 and 2532 respectively.

Referring still to FIG. 3, port 3 of the valve 201 is in fluid communication with the sample delivery module 400 via a fluid path 2522.

Referring to FIG. $4_{1\text{-}2/11\text{-}12}$, ports 17 and 20 of the valve 202 are connected via a fluid holding device (e.g., loops, chips, pipes, etc.) 225.

Referring still to FIG. $4_{1\text{-}2/11\text{-}12}$, ports 11 and 14 of the valve 202 are connected via a fluid holding device (e.g., loops, chips, pipes, etc.) 226.

Referring still to FIG. $4_{1\text{-}2/11\text{-}12}$, ports 6 and 9 of the valve 201 are connected via a fluid holding device (e.g., loops, chips, pipes, etc.) 227.

Referring still to FIG. $4_{1\text{-}2/11\text{-}12}$, the valves 201 and 202 assume at least four discrete configurations. In some embodiments, the valve 201 assumes a configuration in which specific pairs of ports (e.g., 1 and 2, 3 and 4, 5 and 6, 7 and 8, 9 and 10) are in fluid communications. This configuration is described with a subscript to the figure (e.g., $_{1\text{-}2}$) and is a 'load' configuration. In this Figure, the valve 201 is in a 'load' configuration.

Referring still to FIG. $4_{1\text{-}2/11\text{-}12}$, in some embodiments, the valve 202 assumes a configuration in which specific pairs of ports (e.g., 11 and 12, 13 and 14, 15 and 16, 17 and 18, 19 and 20) are in fluid communications. This configuration is described with a subscript to the figure (e.g., $_{11\text{-}12}$) and is a 'load' configuration.

Referring still to FIG. $4_{1\text{-}2/11\text{-}12}$, in some embodiments, the valve 201 and 202 both independently assume 'load' configurations. This is generally labelled as $_{1\text{-}2/11\text{-}12}$.

Referring still to FIG. $4_{1\text{-}2/11\text{-}12}$, in some embodiments, the reactor module 100 is connected to the sample processing module 300 via the filtration module 203 and the fluid holding device 227. In this 'load' configuration of the valve 201, fluid from the reactor module 100 is filtered in the filtration module 203 first before entering into the fluid holding device 227. The direction of the fluidic motion in the filtration module 203 is from port 2 to port 5.

Referring still to FIG. $4_{1\text{-}2/11\text{-}12}$, in some embodiments, the fluid moving device 253 and 254 are capable of transporting fluidic additive(s) to the fluid holding devices 225 and 226 respectively.

Referring still to FIG. $4_{1-2/11-12}$, in some embodiments, at least a portion of the fluid holding devices (225, 226, and 227) is filled with fluid; the fluid in the fluid holding device 227 is filtered.

Referring to FIG. $5_{1-10/11-20}$, in some embodiments, the valve 201 assumes at least one more configuration in which specific pairs of ports (e.g., 1 and 10, 2 and 3, 4 and 5, 6 and 7, 8 and 9) are in fluid communications. This configuration is described with a subscript to the figure (e.g., $_{1-10}$) and is an 'inject' configuration.

Referring still to FIG. $5_{1-10/11-20}$, the valve 202 assumes at least one more configuration in which specific pairs of ports (e.g., 11 and 20, 12 and 13, 14 and 15, 16 and 17, 18 and 19) are in fluid communication. This configuration is described with a subscript to the figure (e.g., $_{11-20}$) and is an 'inject' configuration.

Referring still to FIG. $5_{1-10/11-20}$, in some embodiments, the valve 201 and 202 both independently assume 'inject' configurations. This is generally labelled as $_{1-10/11-20}$.

Referring still to FIG. $5_{1-10/11-20}$, the reactor module 100 is in fluid communication with the sample processing module 300 via ports 1 and 10.

Referring still to FIG. $5_{1-10/11-20}$, in some embodiments, the filtration module 203 is in fluid communication with the fluid moving device 252, but the direction of flow in the filtration module 203 is opposite (i.e., from port 5 to port 2) to the direction of flow when the valve 201 is set in the 'load' configuration (i.e., from port 2 to the port 5).

Referring still to FIG. $5_{1-10/11-20}$, in some embodiments, the fluid moving device 251 is in fluid communication with the sample delivery module 400 via the fluid holding devices 226, 225, and 227. In this configuration, the fluid moving device 251 is capable of transporting the fluidic additive(s) from the valve 202 and the isolated filtrate from the valve 201 to the sample delivery module 400.

Referring still to FIG. $5_{1-10/11-20}$, in some embodiments, the sample delivery module 400 is capable of transporting the fluidic additive(s) from the valve 202 and the isolated filtrate from the valve 201 to the sample analysis module 500.

Referring to FIG. $6_{1-10/11-12}$, in some embodiments, the valve 201 is in an 'inject' configuration in which the ports 1 and 10 are in fluid communication and the valve 202 is in a 'load' configuration in which the ports 11 and 12 are in fluid communication. This configuration is generally labelled as $_{1-10/11-12}$.

Referring still to FIG. $6_{1-10/11-12}$, in some embodiments, the filtration module 203 is in fluid communication with the fluid moving device 252 and the direction of flow is set to be opposite (i.e., from port 5 to port 2) to the direction of flow when the sampling valve 201 is set in a 'load' configuration (i.e., from port 2 to the port 5). In this configuration, the fluid moving device 252 is capable of transporting the residue from the filtration module 203 to the sample delivery module 400.

Referring still to $6_{1-10/11-12}$, in some embodiments, the sample delivery module 400 is capable of transporting the residue to the sample analysis module 500.

Referring still to FIG. $6_{1-10/11-12}$, in some examples, the fluid moving device 251 is in fluid communication with the sample delivery module 400 via the fluid holding device 227, but not via 225 and 226. In this configuration, the fluid holding devices 225 and 226 are being with the fluidic additives by the fluid moving device 253 and 254, respectively.

Referring to FIG. $7_{1-2/11-20}$, the valve 201 is in a 'load' configuration and the valve 202 is in an 'inject' configuration. This is generally labelled as $_{1-2/11-20}$.

Referring still to FIG. $7_{1-2/11-20}$, in some embodiments, the fluid moving device 251 is in fluid communication with the sample delivery module 400 via the fluid holding devices 225 and 226, but not via 227. In this configuration, the fluid moving device 251 is capable of moving the fluidic additive(s) from the fluid holding devices 225 and 226 of the valve 202 toward the sample delivery module 400. In some examples, this configuration is used for quantification of fluidic additive(s).

Referring to FIG. $8_{1-2/11-12}$, the valve 201 is in a 'load' configuration and the valve 202 is in an 'inject' configuration. This is generally labelled as $_{1-2/11-12}$.

Referring still to FIG. $8_{1-2/11-12}$, in some embodiments, the filtration module includes an inline filter 206. In this configuration, the reactor module 100 is connected to the sample processing module 300 via the inline filter 206 and the fluid holding device 227; the direction of flow in the inline filter 206 is from port 2 to port 5.

Referring to FIG. $9_{1-10/11-12}$, in some embodiments, the reactor module 100 is connected to the sample processing module 300 via ports 1 and 10. The inline filter 206 is in fluid communication with the fluid moving device 252 and the direction of flow in the inline filter 206 is from port 5 to port 2.

Referring to FIG. $10_{1-10/11-12/21-22}$, in some embodiments, ports 3 and 4 of valve 201 are connected to ports 22 and 24 of a multi-port valve 207 via flowpaths 25221 and 2521, respectively; port 21 of multi-port valve 207 is connected to sample delivery module 400 via flowpath 25222; fluid moving module 261 is connected to valve 207 at port 23. Valve 207 assumes configuration in which specific pairs of ports (21 and 22, 23 and 24) are in fluid communications. This configuration is labelled as $_{21-22}$. In this configuration, fluid moving device 261 is in fluid communication with inline filter 206 and the direction of flow is from port 5 to port 2.

Referring to FIG. $11_{1-10/11-12/21-24}$, in some embodiments, ports 3 and 4 of valve 201 are connected to ports 22 and 24 of a multi-port valve 207 via flowpaths 25221 and 2521, respectively; port 21 of multi-port valve 207 is connected to sample delivery module 400 via flowpath 25222; fluid moving module 261 is connected to valve 207 at port 23.

Valve 207 assumes configuration in which specific pairs of ports (21 and 24, 22 and 23) are in fluid communications. This configuration is labelled as $_{21-24}$. In this configuration, fluid moving device 261 is in fluid communication with inline filter 206, but the direction of flow is from port 2 to port 5 (i.e., in the same direction as the direction of flow when the sampling valve 201 is set in the 'load' configuration without valve 207).

Referring to FIG. 12, in some embodiments, the sampling module is a multi-ring valve 204. The configurable part of the valve 204, which is referred to as the 'rotor', hosts multiple arrays of configurable flowpaths (e.g., slits or channels).

Referring still to FIG. 12, in some embodiments, the configurable flowpaths are distributed in concentric rings (circles) on the rotor of the valve 204.

Referring still to FIG. 12, in some embodiments, configurable flowpaths distributed among different rings (circles) uniformly. For example, in this Figure, ten configurable flowpaths are distributed in two concentric rings (circles) with each circle comprising five slits and the angular distances between any two adjacent slits in a ring are same.

Referring to still FIG. 12, in some embodiments, the valve 204 is a two-position valve.

Referring to still FIG. 12, in some embodiments, the reactor module 100 is connected to port 1 via the fluid path 1001 and the sample processing module 300 is connected to port 10 via the fluid path 1002. The sample delivery module 400 is connected to the valve 204 at port 8. The filtration module 203 is connected to the valve 204 via ports 2 and 5.

Figure 13:
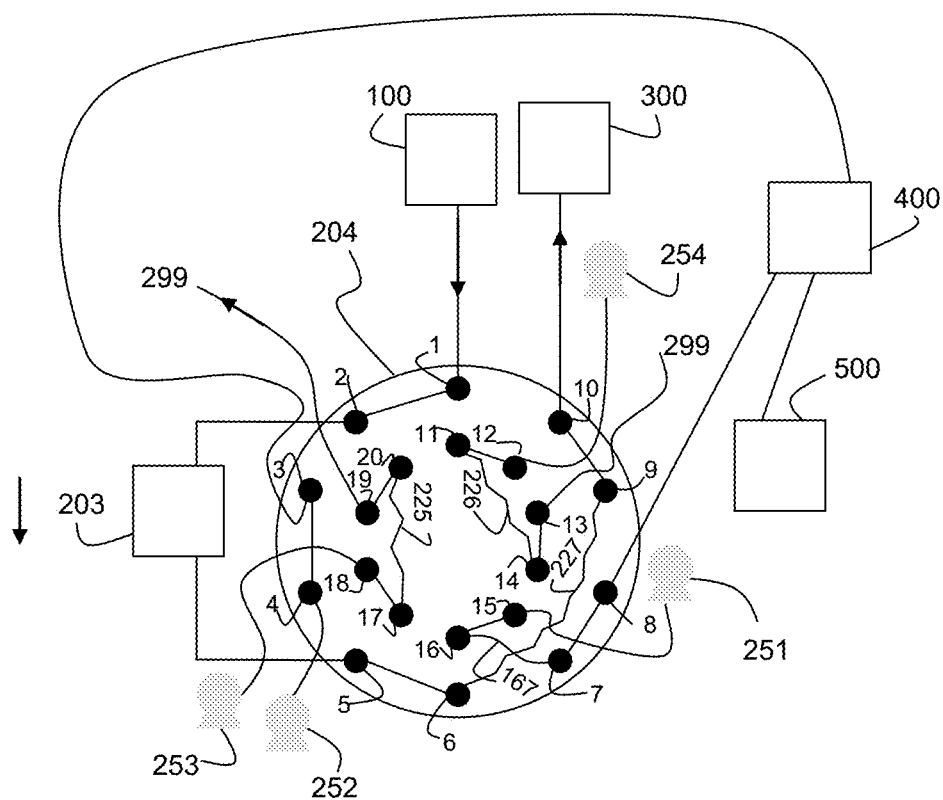

Referring to FIG. 13$_{1-2/(11-20)}$, in some embodiments, the valve 204 assumes a configuration in which specific pair of ports (1 and 2, 3 and 4, 5 and 6, 7 and 8, 9 and 10, 11 and 12, 13 and 14, 15 and 16, 17 and 18, 19 and 20) are in fluid communications. This configuration is labelled as $_{1-2/(11-12)}$. It is imperative that, in this example, when the ports 1 and 2 are in fluid communication, the ports 11 and 12 are also in fluid communication. The secondary connectivity (e.g., between ports 11 and 12) is indicated for clarity and is shown in parenthesis. This is a 'load' configuration of the valve 204.

Referring still to FIG. 13$_{1-2/(11-12)}$, in some embodiments, the fluid moving devices 251, 252, 253, and 254 are connected at ports 15, 4, 18, and 12, respectively.

Referring still to FIG. 13$_{1-2/(11-12)}$, in some embodiments, ports 17 and 20 are connected by the fluid holding device 225.

Referring still to FIG. 13$_{1-2/(11-12)}$, in some embodiments, ports 11 and 14 are connected by the fluid holding device 226.

Referring still to FIG. 13$_{1-2/(11-12)}$, in some embodiments, ports 6 and 9 are connected by the fluid holding device 227.

Referring still to FIG. 13$_{1-2/(11-12)}$, in some embodiments, the filtration module 203 is connected to the valve 204 between ports 2 and 5.

Referring still to FIG. 13$_{1-2/(11-12)}$, port 7 and 16 are connected by a fluid path 167.

Referring still to FIG. 13$_{1-2/(11-12)}$, in some embodiments, the reactor module 100 is in fluid communication with the sample processing module 300 via the filtration module 203 and the fluid holding device 227. In this configuration (load), fluid from the reactor module 100 is filtered in the filtration module 203 first and then the filtrate is moved toward the fluid holding device 227.

Referring still to FIG. 13$_{1-2/(11-12)}$, in some embodiments, the fluid moving devices 253 and 254 are in fluid communications with the fluid holding devices 225 and 226 respectively. In this configuration, in some examples, the fluid moving devices 253 and 254 are capable of introducing the fluidic additives.

Referring still to FIG. 13$_{1-2/(11-12)}$, in some embodiments, the fluid moving device 252 moves fluid toward the sample delivery module 400.

Referring still to FIG. 13$_{1-2/(11-12)}$, in some embodiments, the sample delivery module 400 moves the fluid from the fluid moving device 252 to the sample processing module 500. In alternate examples, the sample delivery module 400 moves the fluid from the fluid moving device 252 to waste.

Referring still to FIG. 13$_{1-2/(11-12)}$, in some embodiments, the sample delivery module 400 is equipped with movable parts and is capable of receiving fluids from the fluid moving devices 251 and 252 in sequence and delivering the fluids to sample analysis module 500 in sequence.

Figure 14:
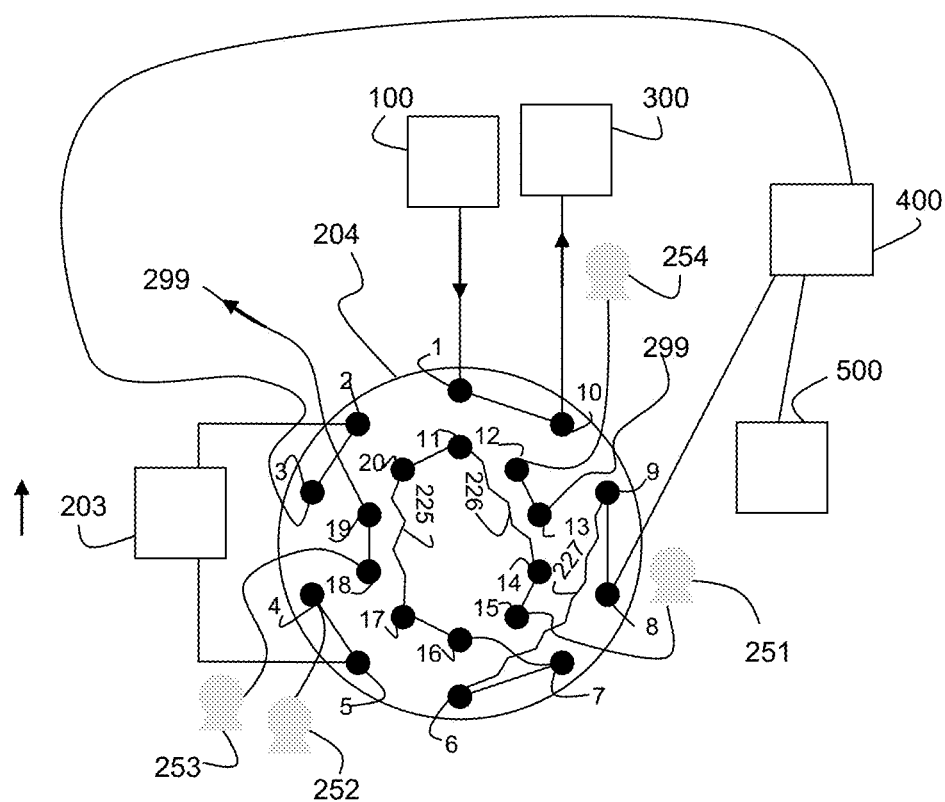

Referring to FIG. 14$_{1-10/(11-20)}$, the valve 204 assumes at least one more configuration in which specific pairs of ports (1 and 10, 2 and 3, 4 and 5, 6 and 7, 8 and 9, 11 and 20, 12 and 13, 14 and 15, 16 and 17, 18 and 19) are in fluid communications. This configuration is labelled as $_{1-10/(11-20)}$. It is imperative that, in this example, when the ports 1 and 10 are in fluid communication, the ports 11 and 20 are also in fluid communication. The secondary connectivity (e.g., between ports 11 and 20) is indicated for clarity and is shown in parenthesis. This is an 'inject' configuration.

Referring still to FIG. 14$_{1-10/(11-20)}$, the fluid moving device 251 is in fluid communication with the sample delivery module 400 via the fluid holding devices 225, 226, and 227. In this configuration (inject), the fluid moving device 251 is capable of moving the fluidic additives (from 225 and 226) and the filtrate (from 227) toward the sample delivery module 400.

Referring still to FIG. 14$_{1-10/(11-20)}$, in some embodiments, the sample delivery module 400 is capable diverting the fluidic additives (from 225 and 226) and the filtrate (from 227) to the sample analysis module 500.

Referring still to FIG. 14$_{1-10/(11-20)}$, in some embodiments, the reactor module 100 is in fluid communication with the sample processing module 300 via the ports 1 and 10.

Referring still to FIG. 14$_{1-10/(11-20)}$, in some embodiments, the filtration module 203 is in fluid communication with the fluid moving device 252 and the direction of fluid motion in the filtration module 203 is opposite (i.e., from port 5 to port 2) to the one when the valve 204 is in the 'load' configuration.

Figure 15:
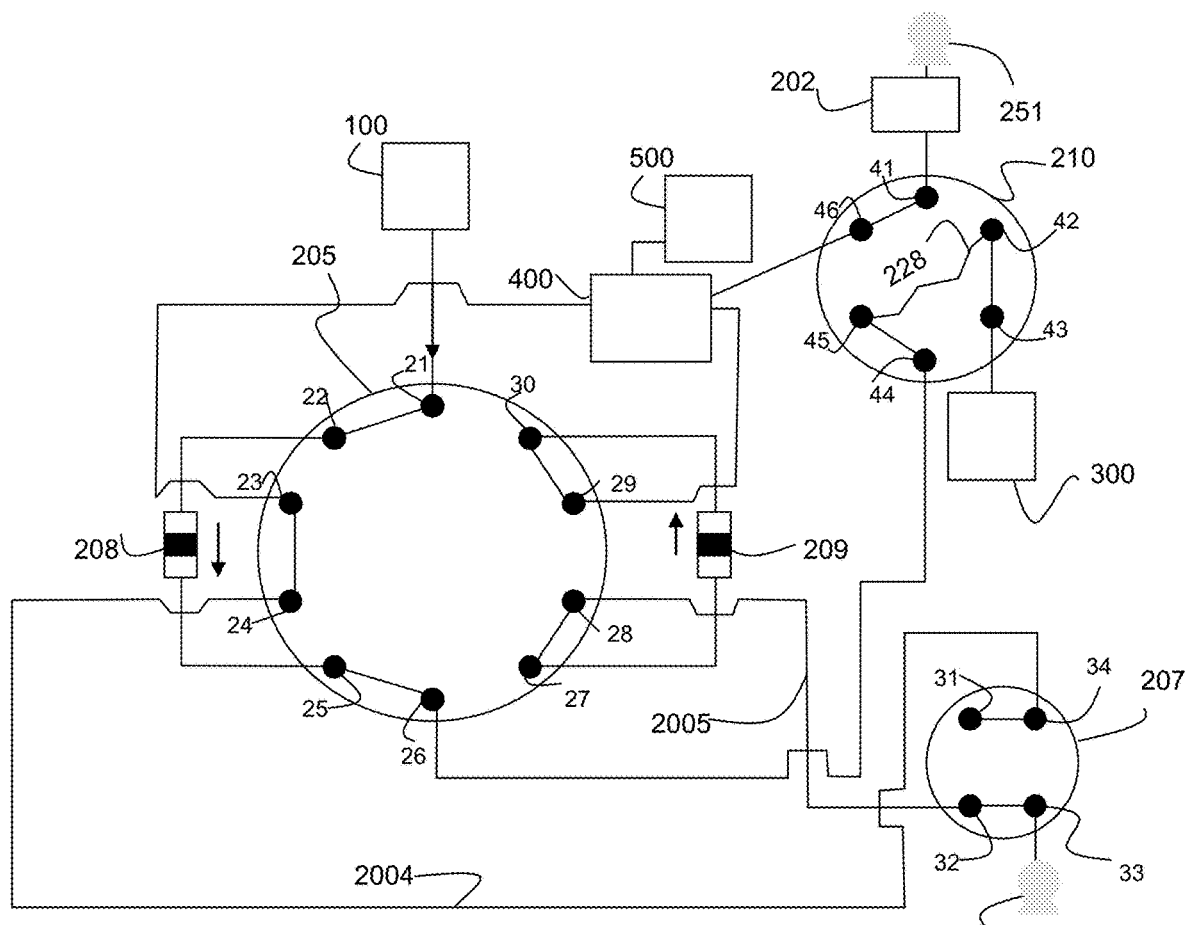
Figure 16:
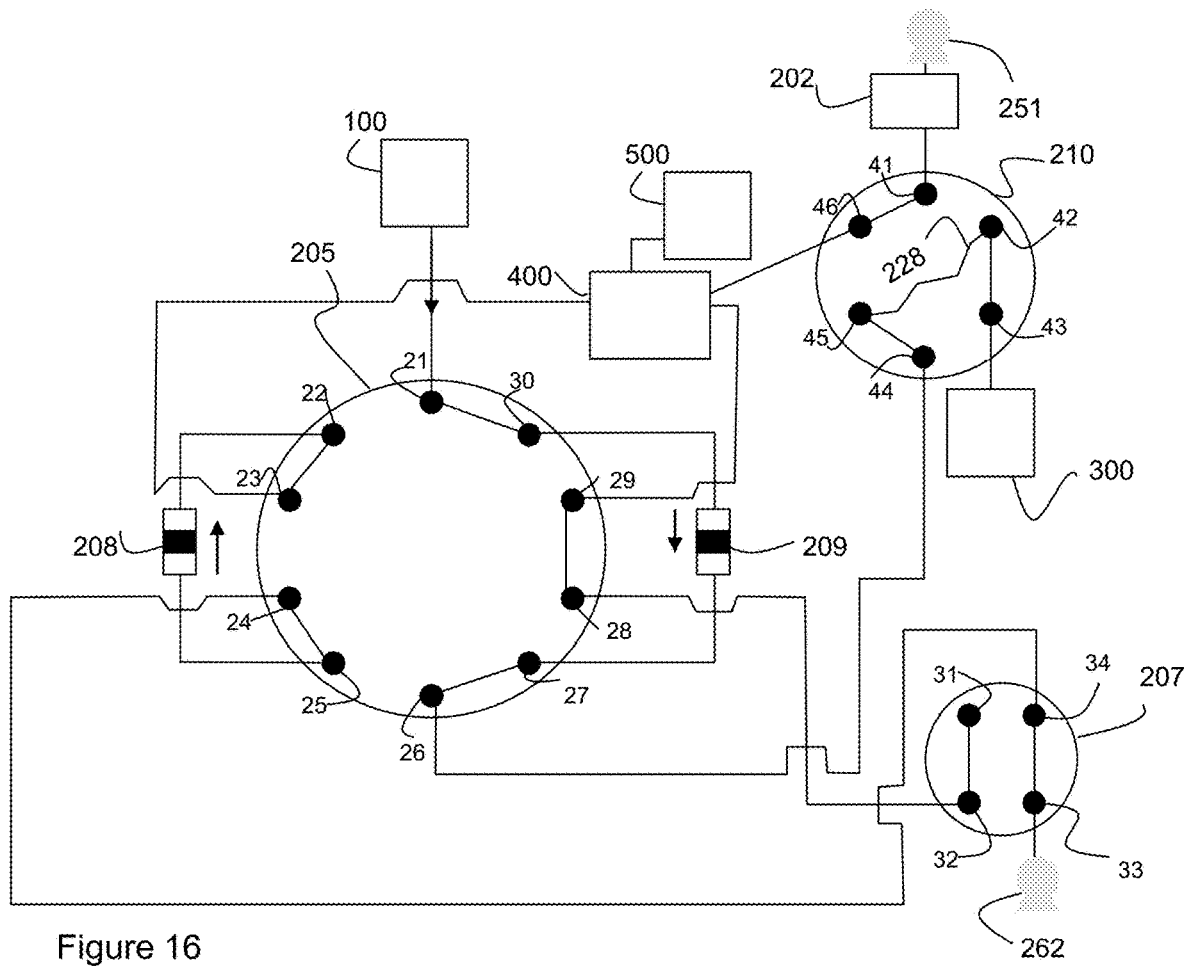
Figure 17:
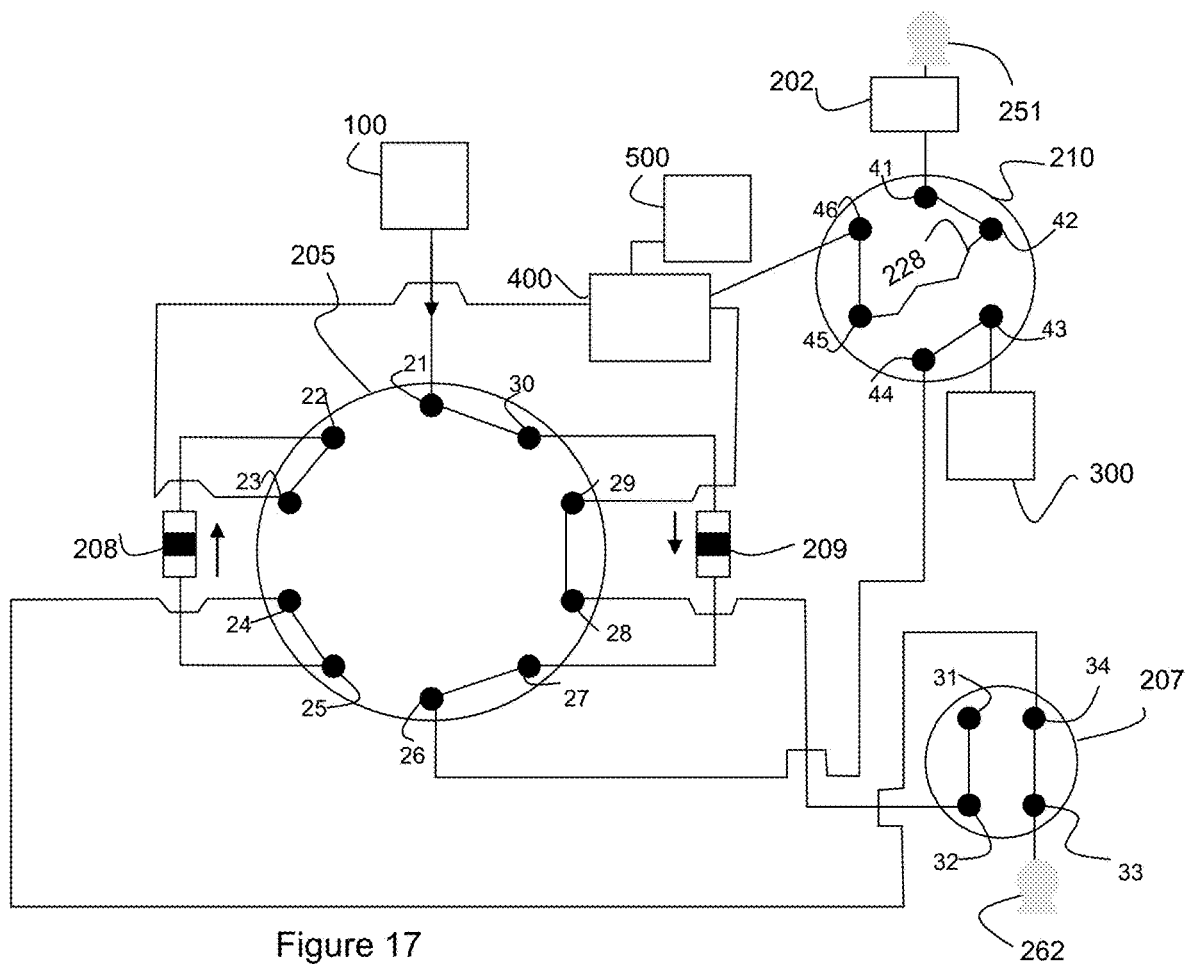
Figure 18:
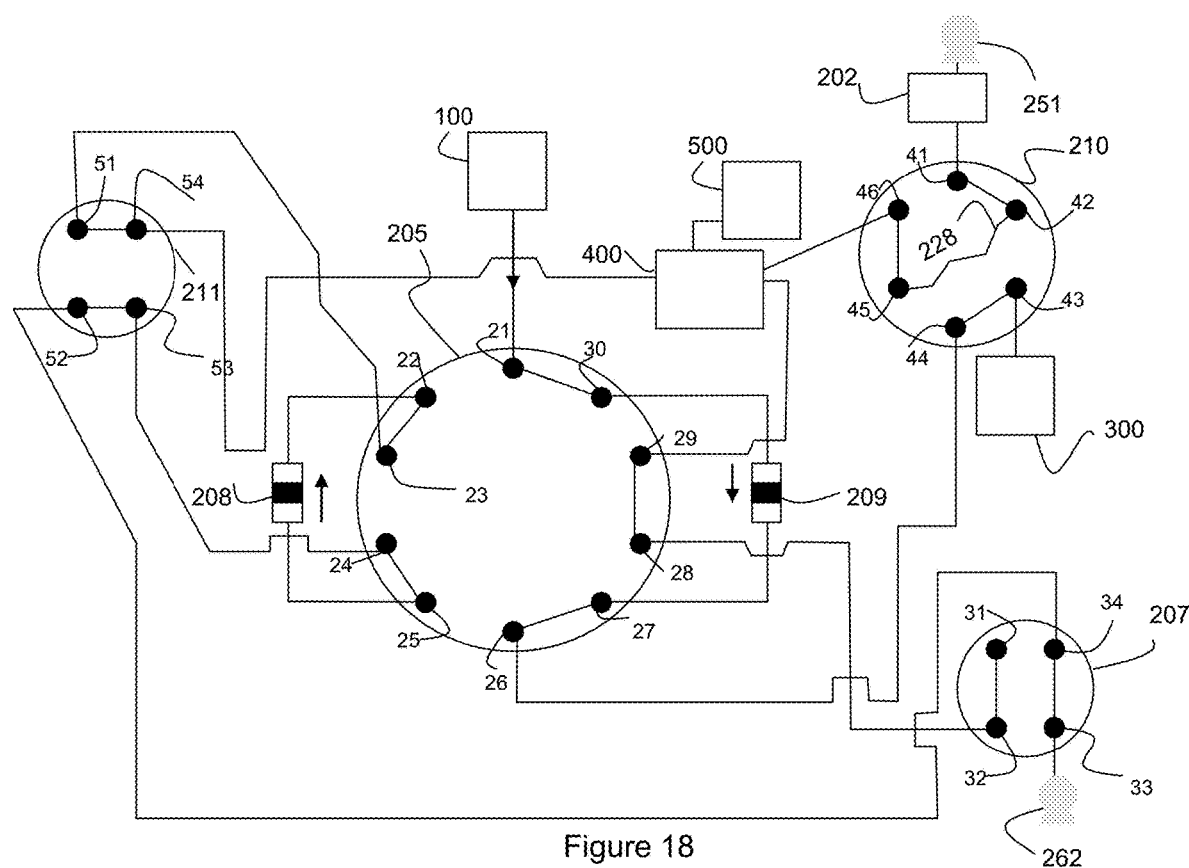
Figure 19:
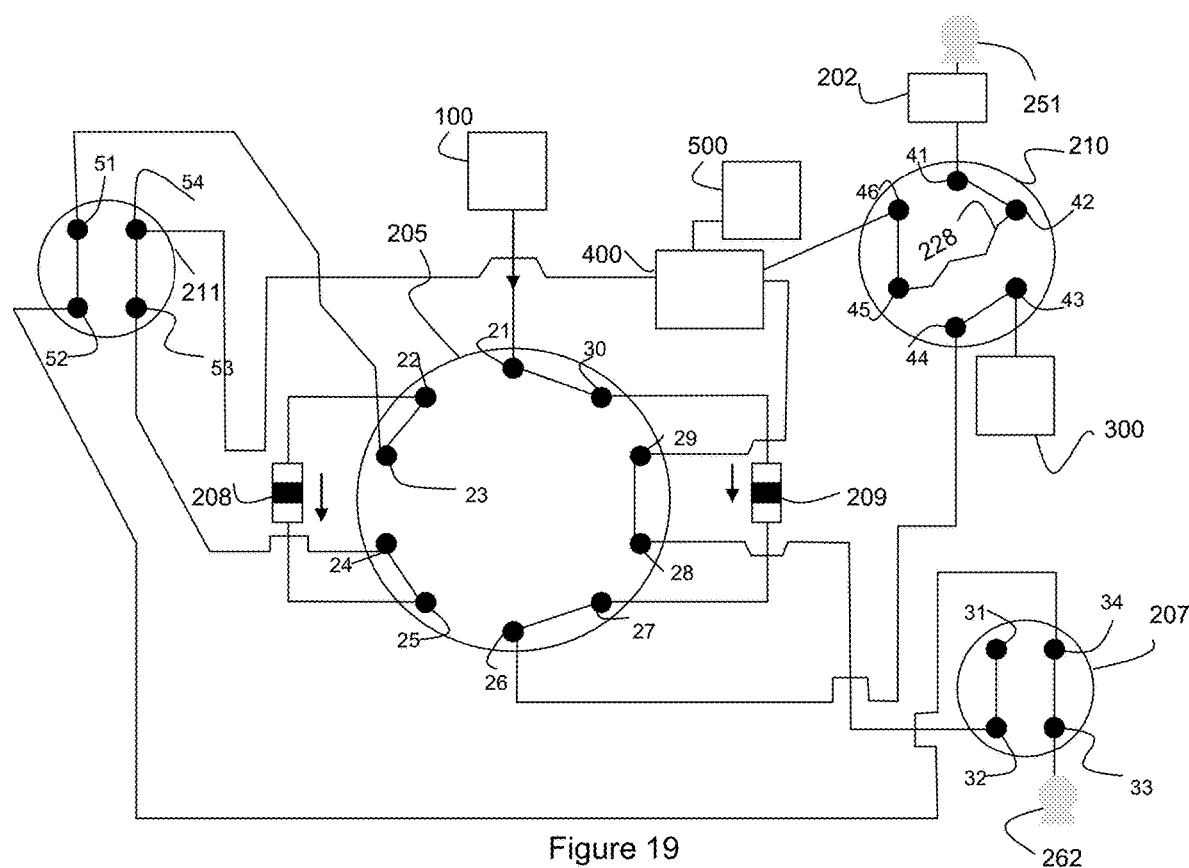
Figure 20:
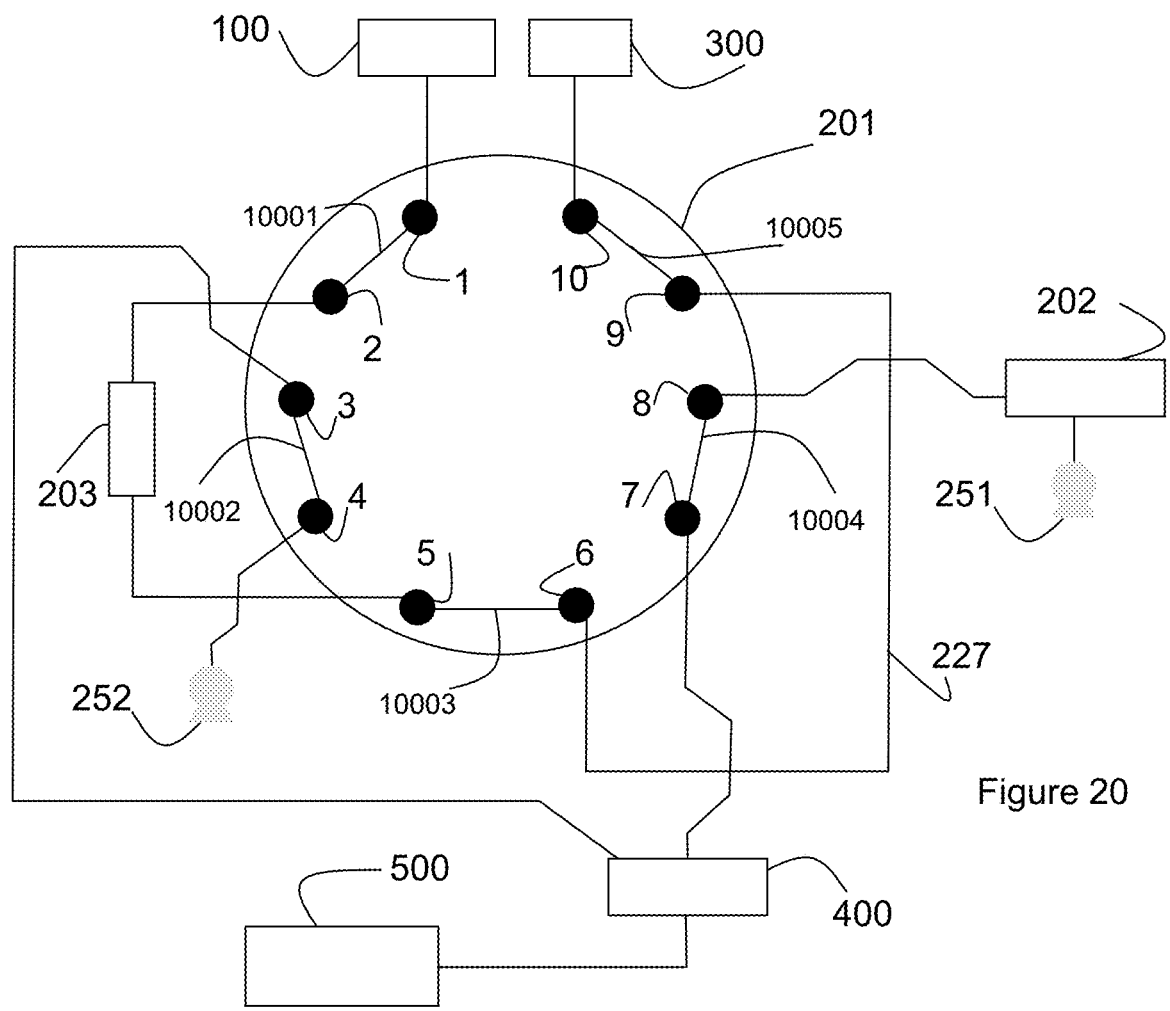
Figure 21:
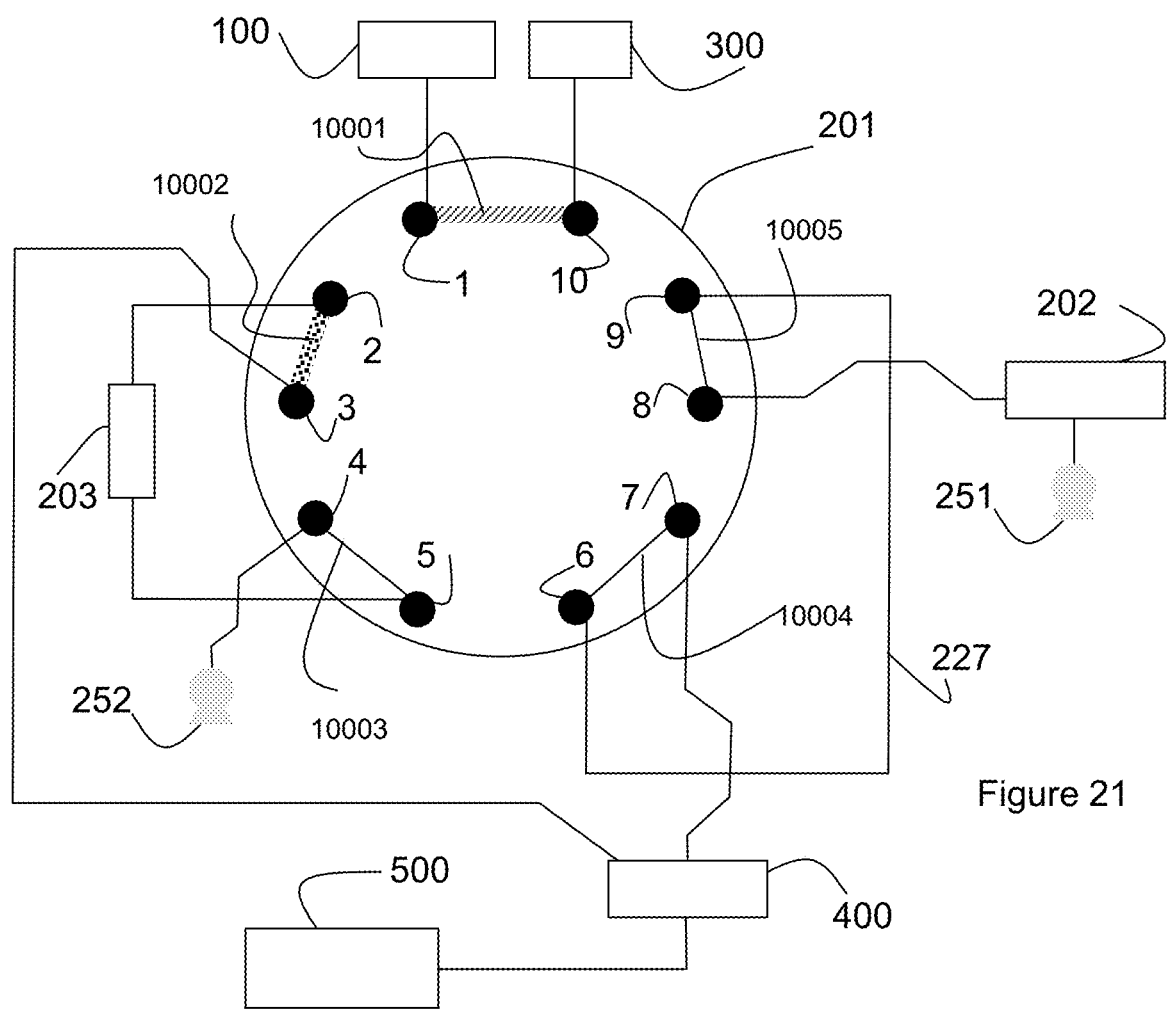
Figure 22:
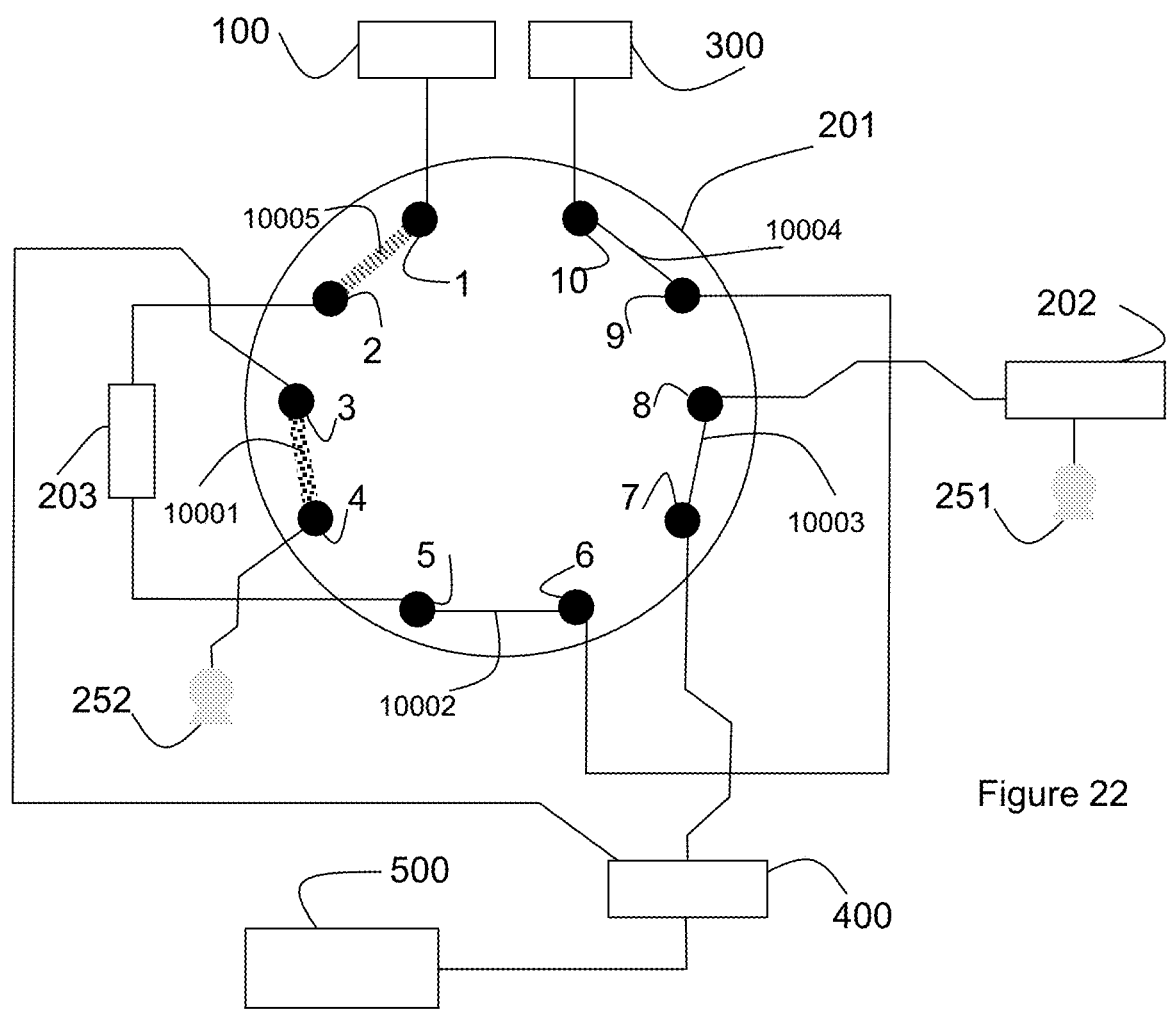
Figure 23:
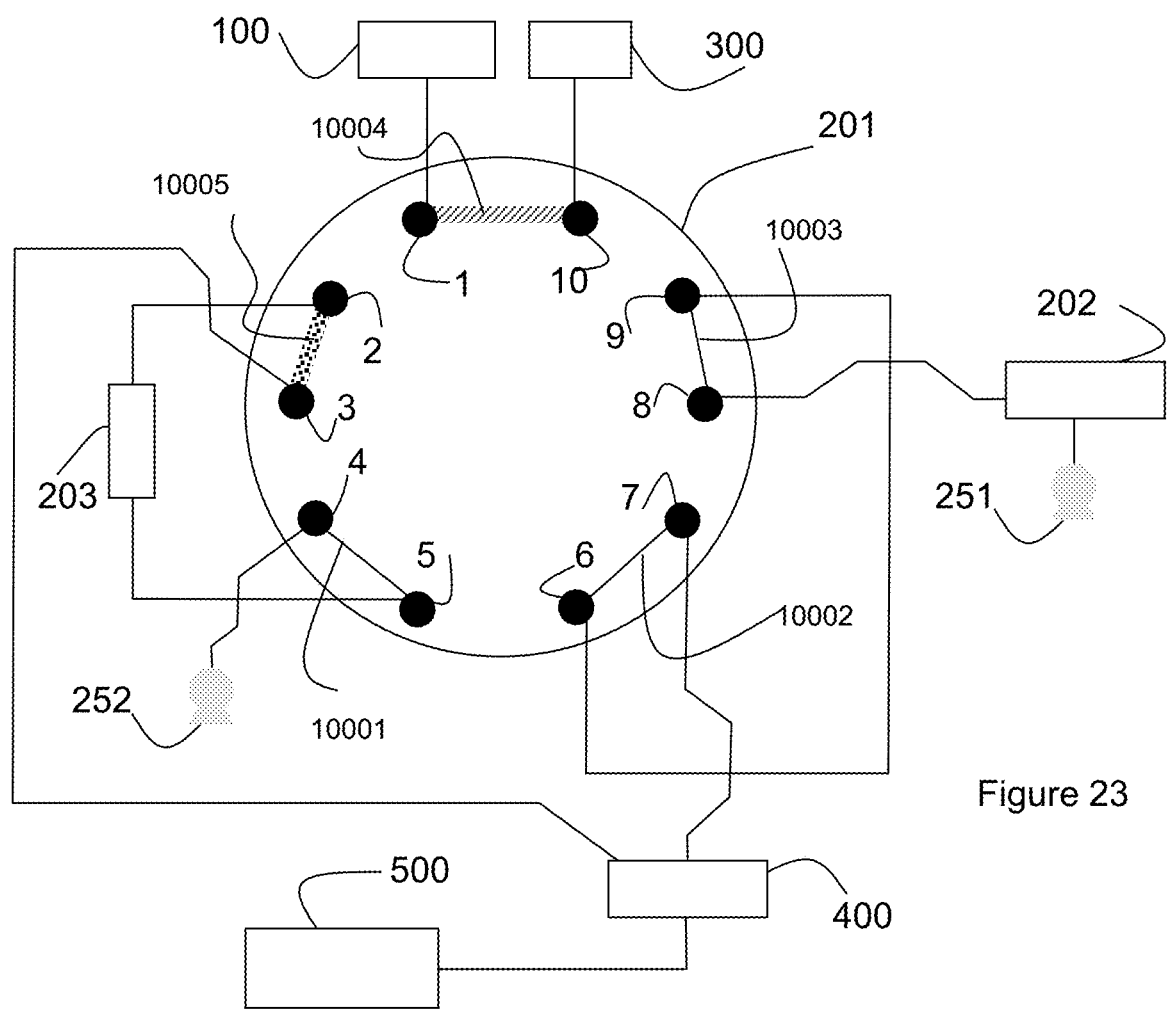
Figure 24:
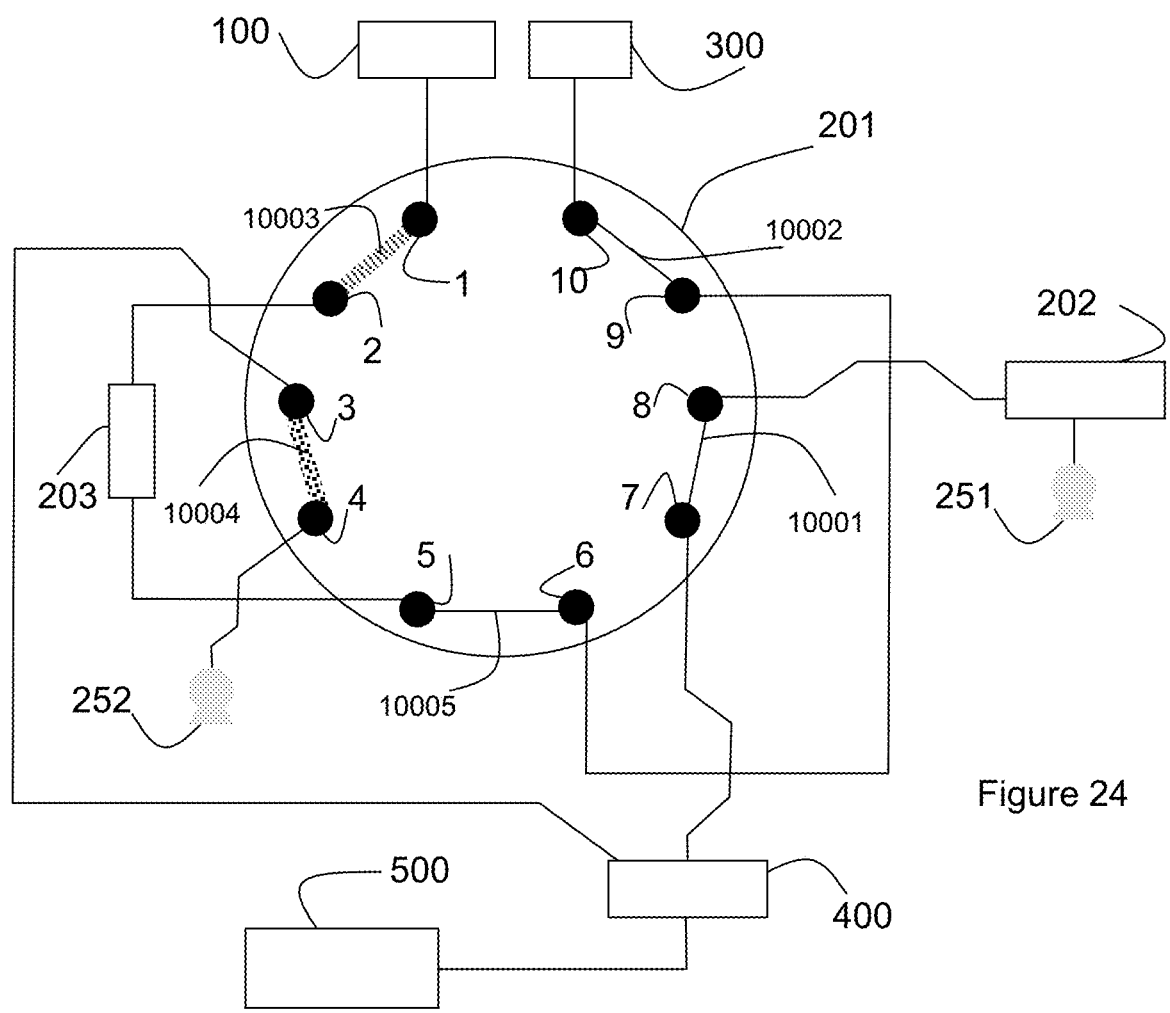
Figure 25:
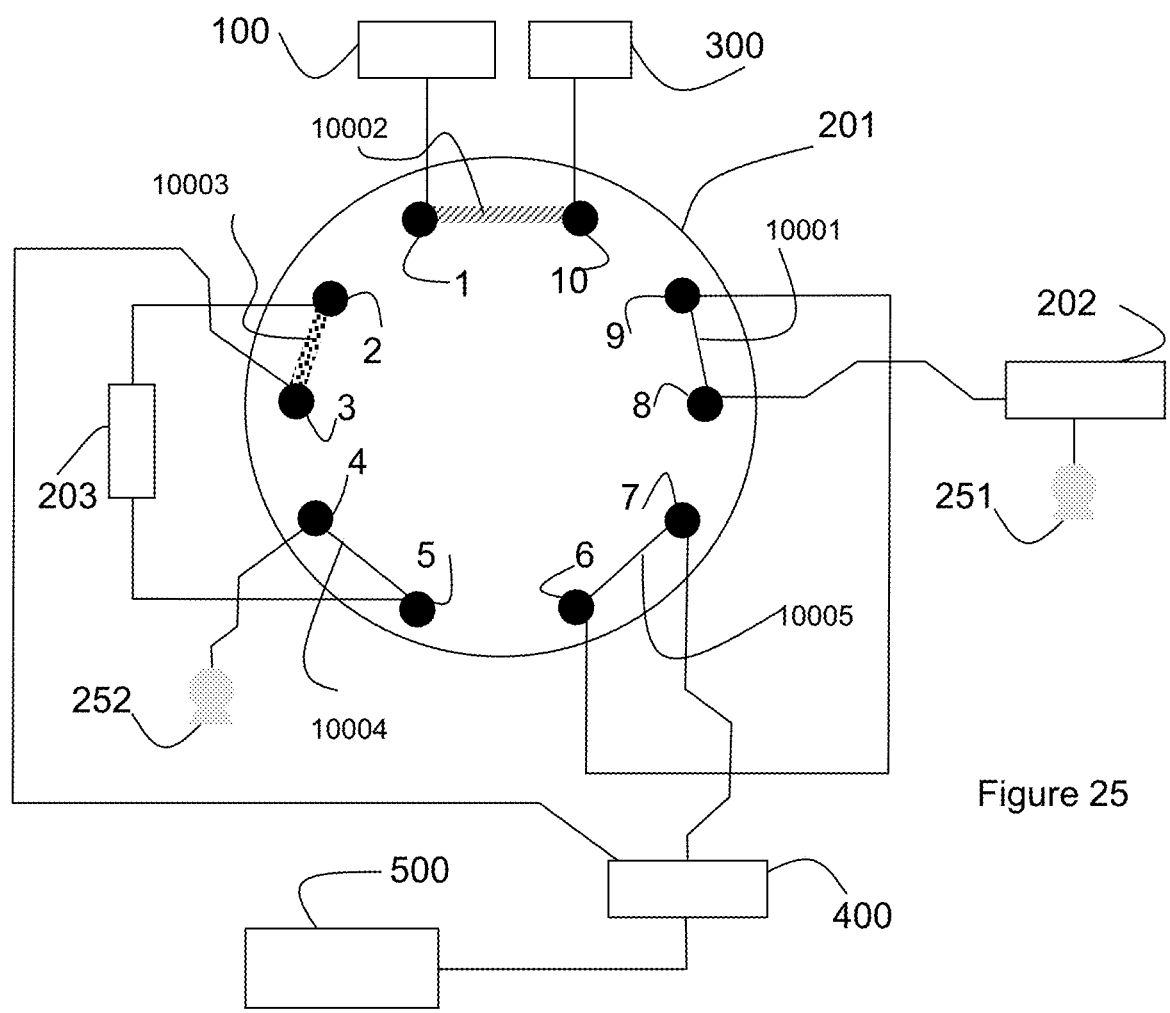
Figure 26:
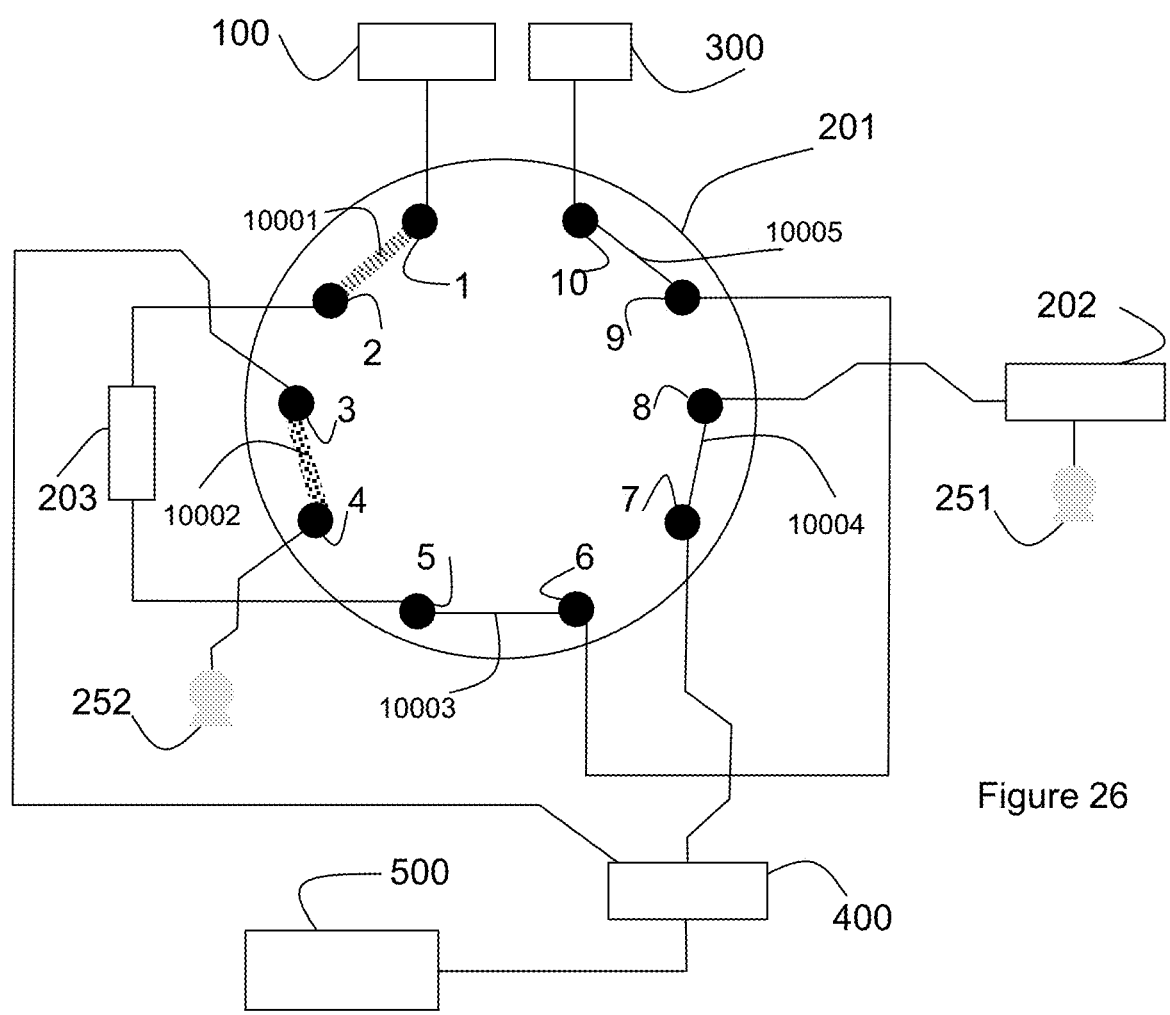
Figure 27:
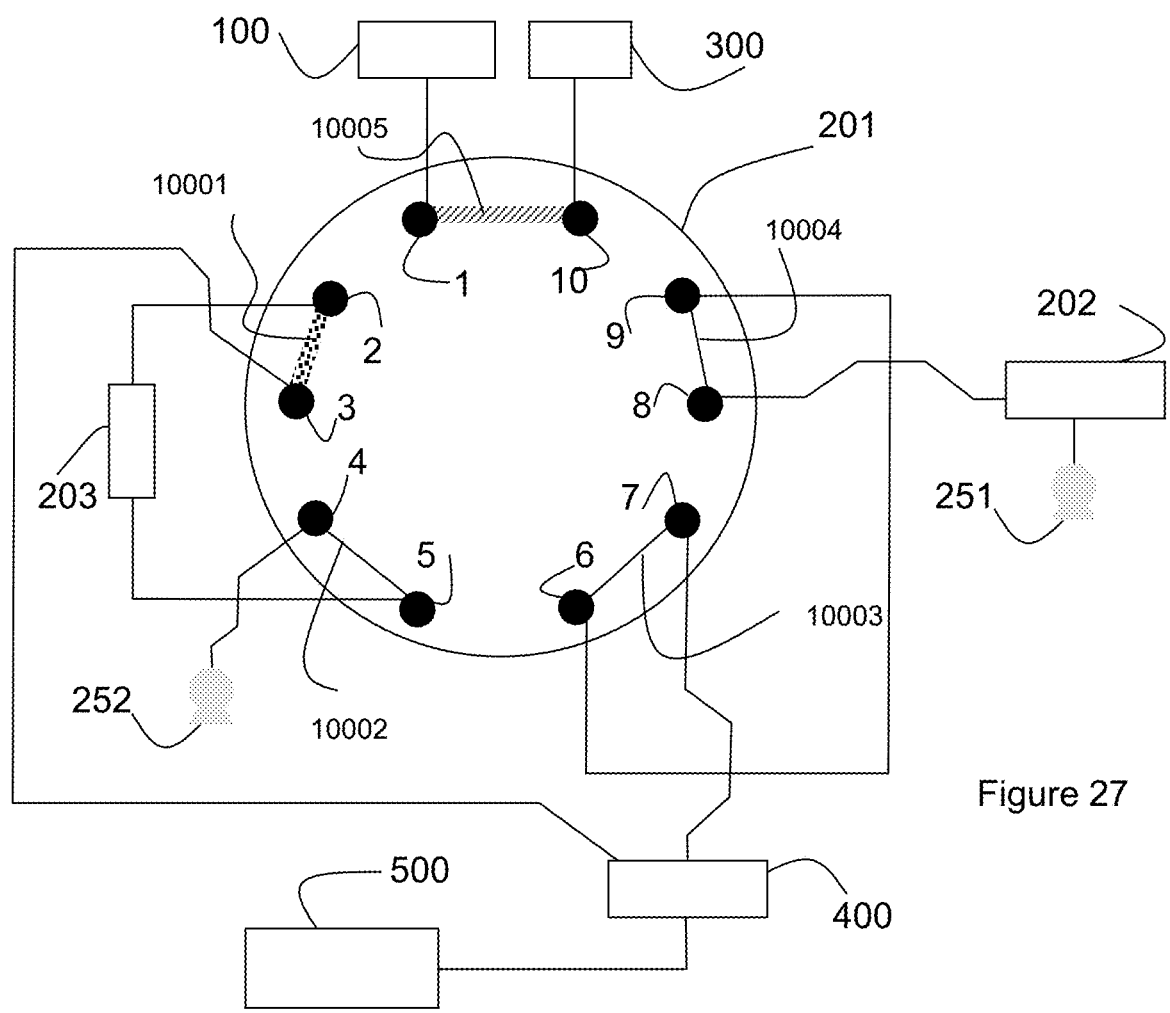
Figure 28:
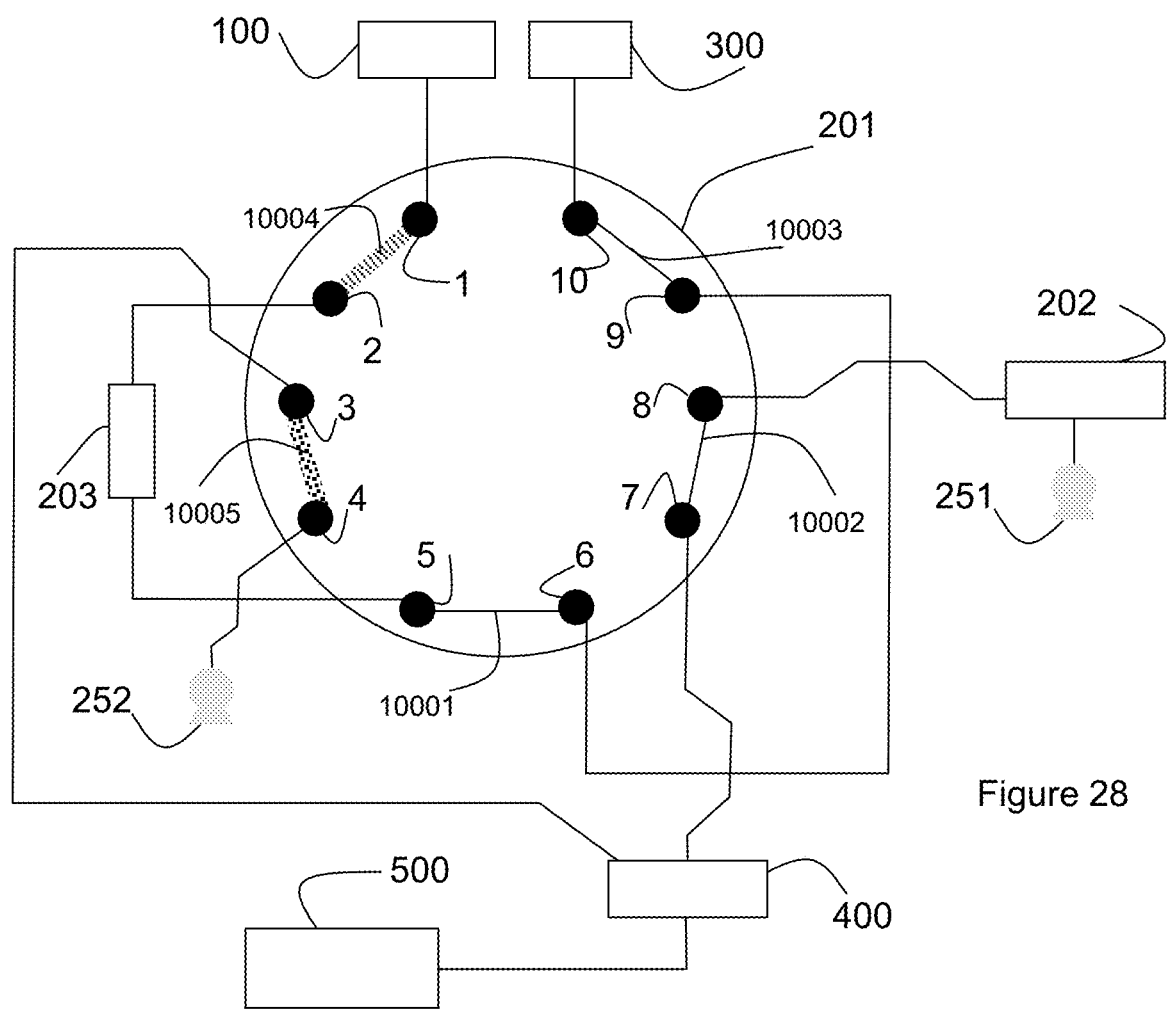
Figure 29:
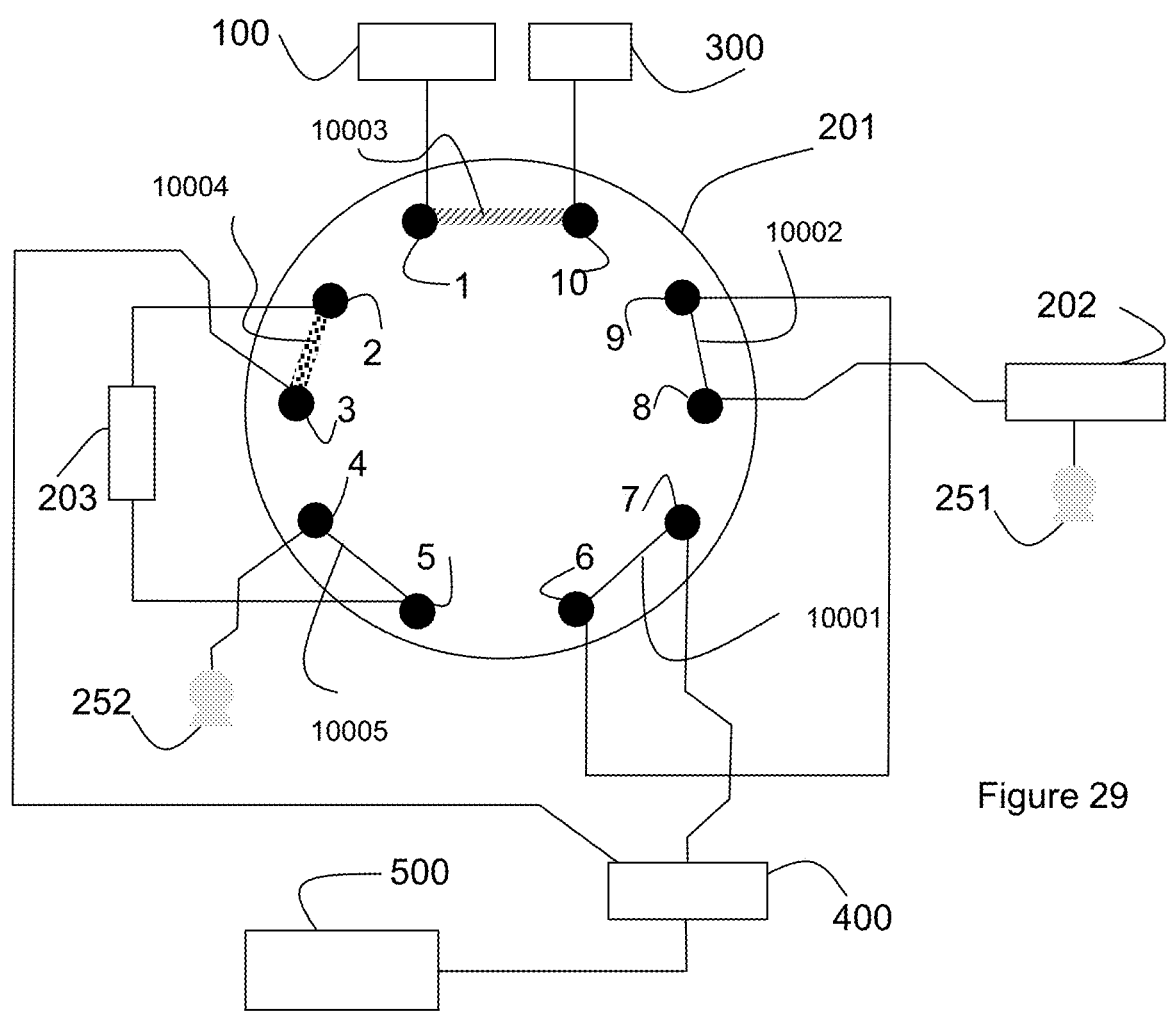
Figure 30:
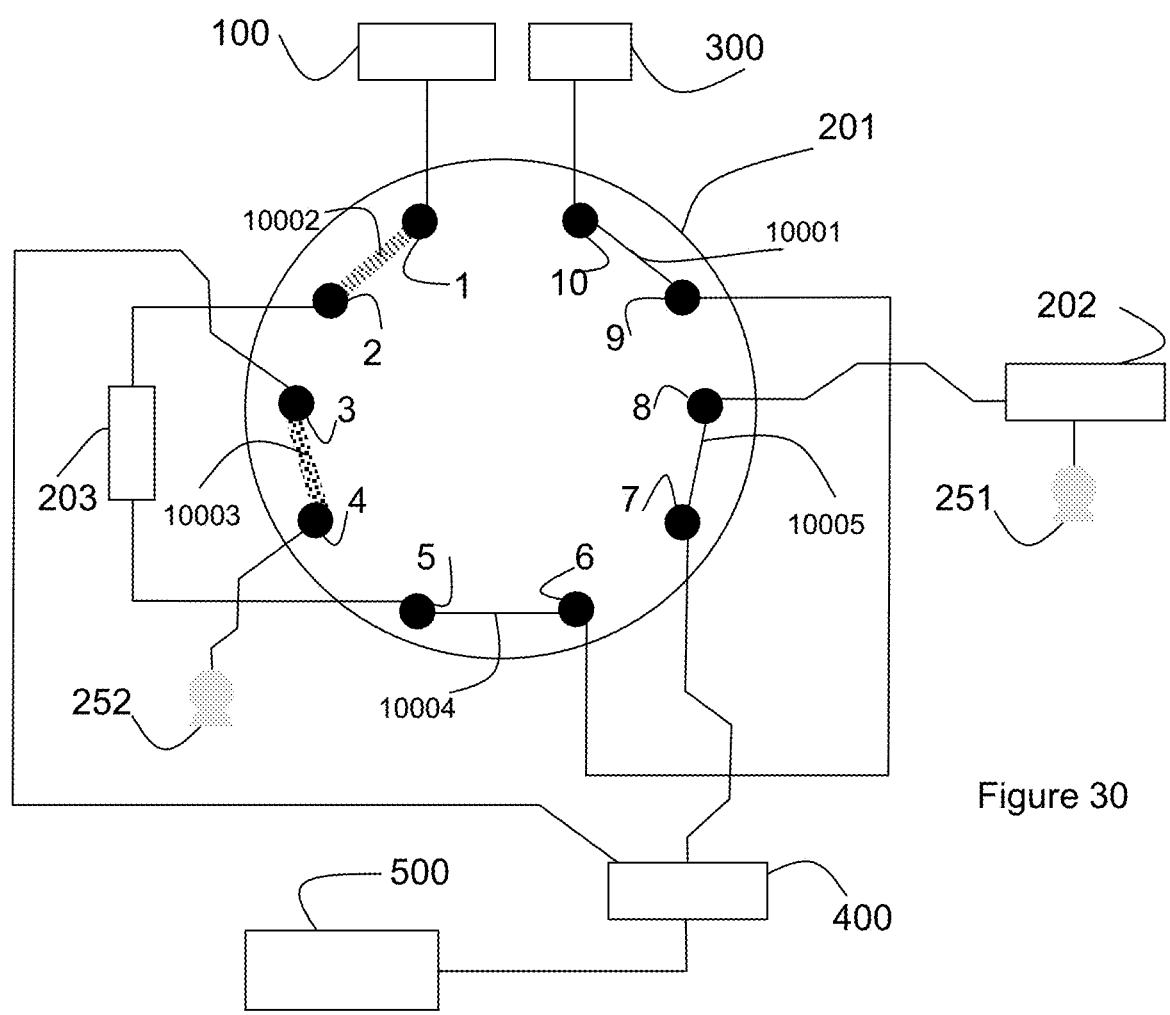
Figure 31:
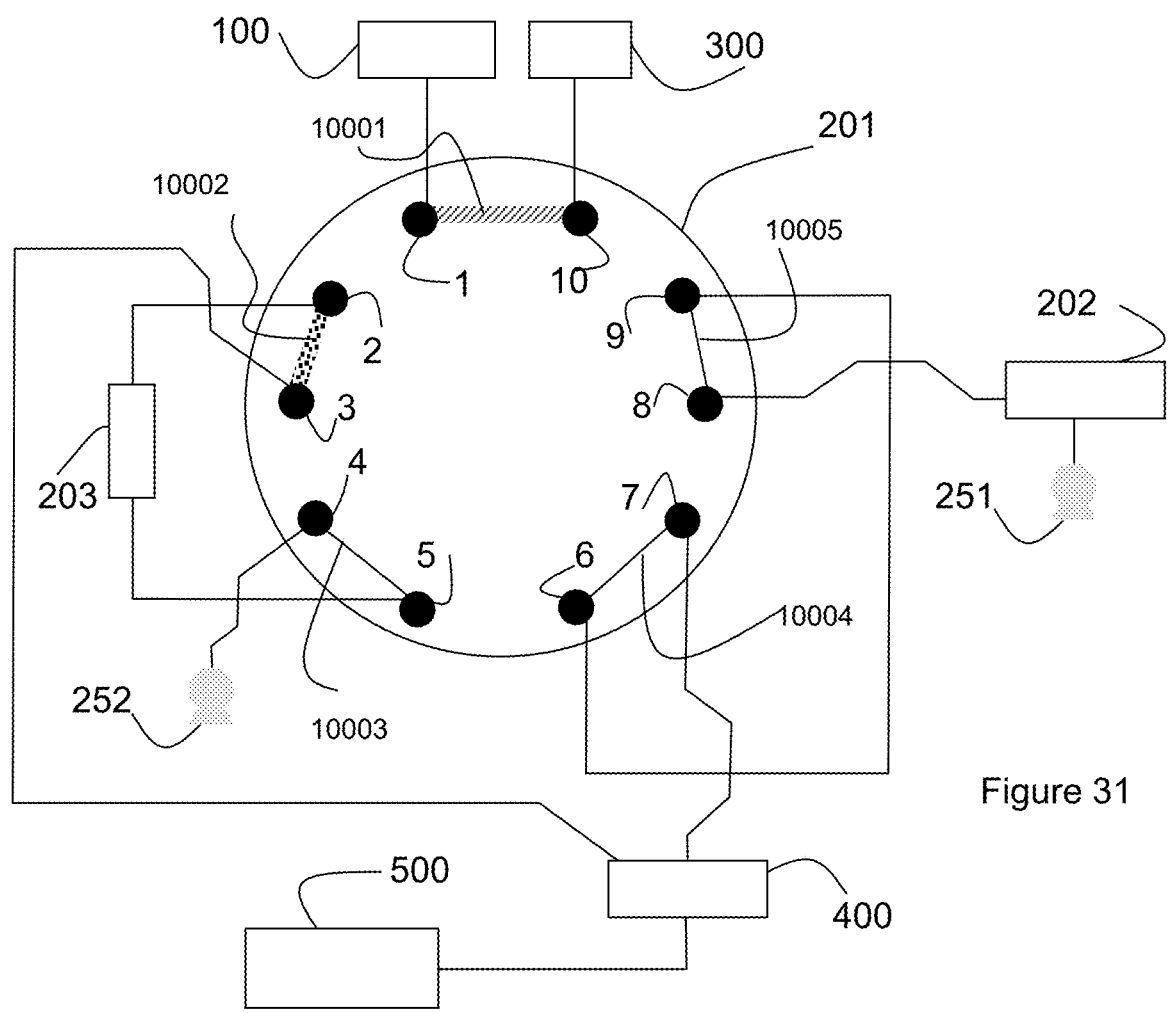
Figure 32:
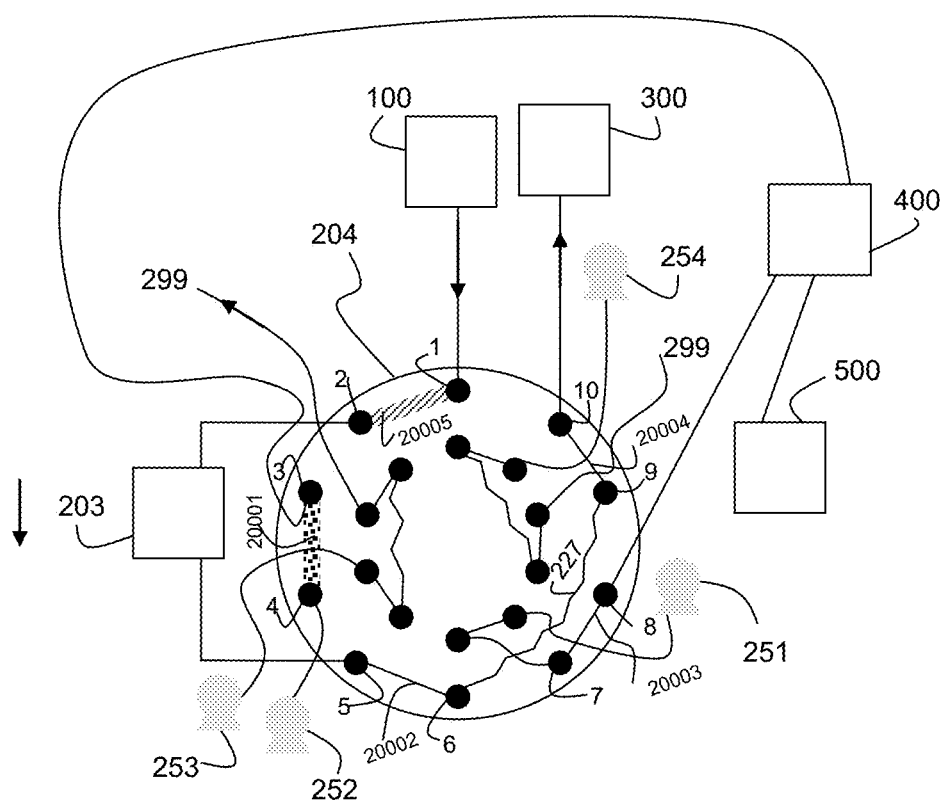
Figure 33:
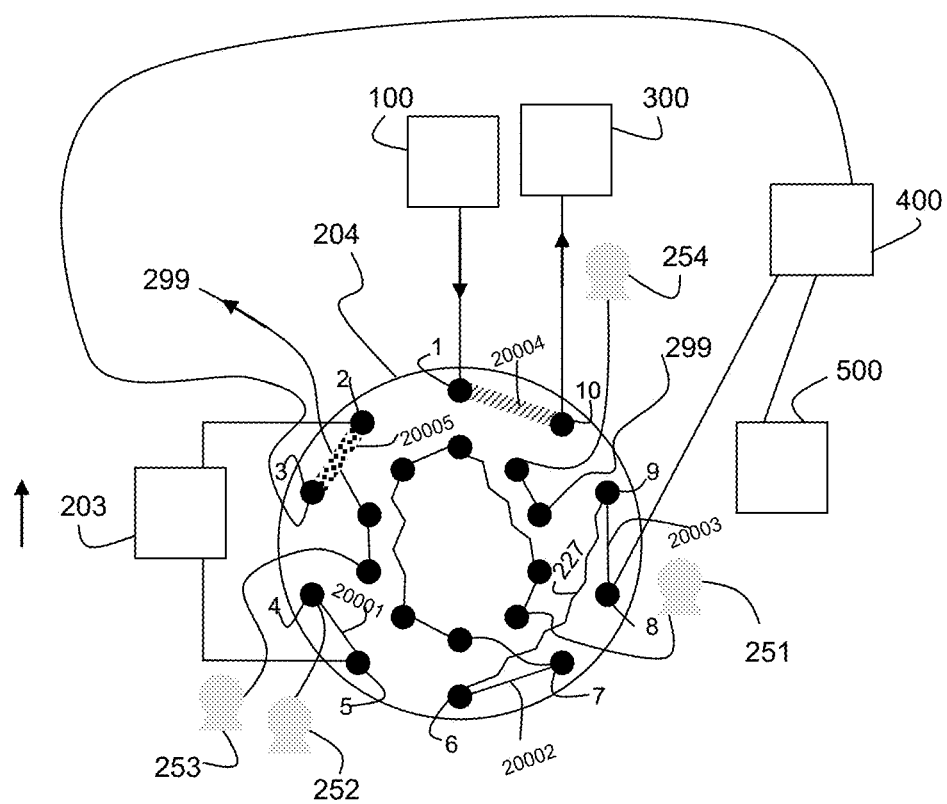
Figure 34:
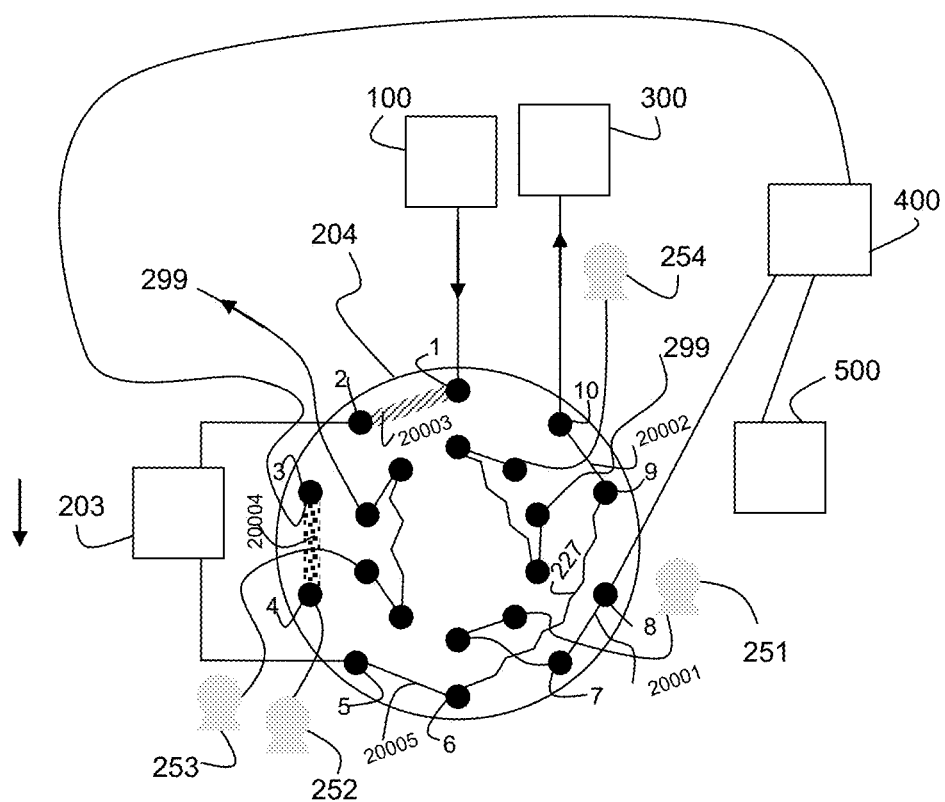
Figure 35:
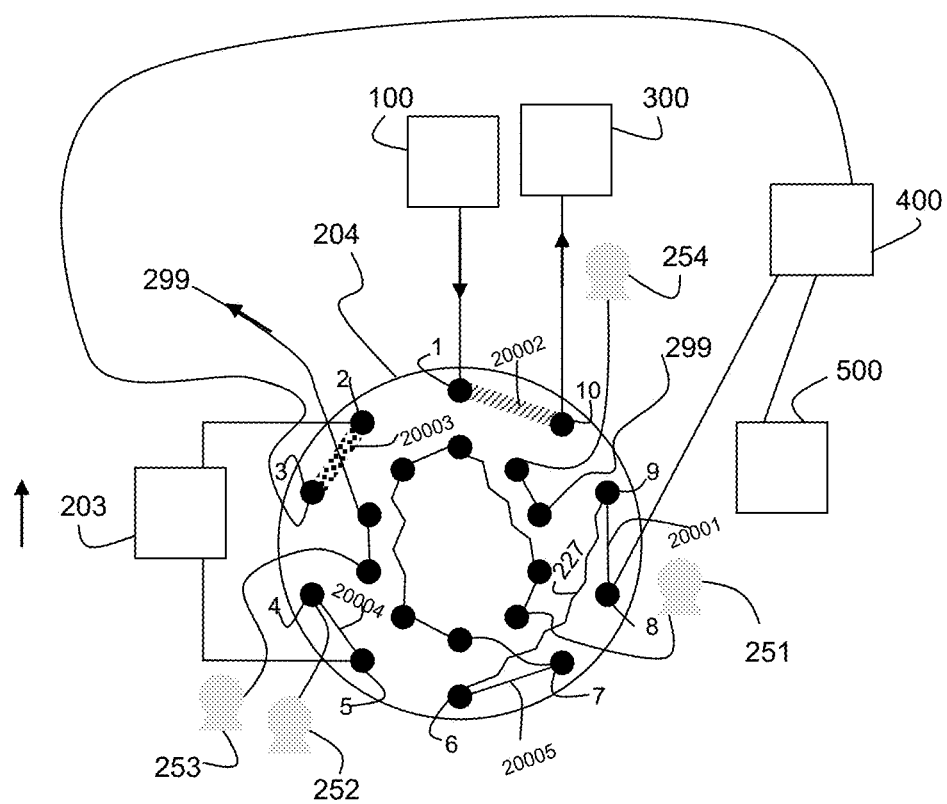
Figure 36:
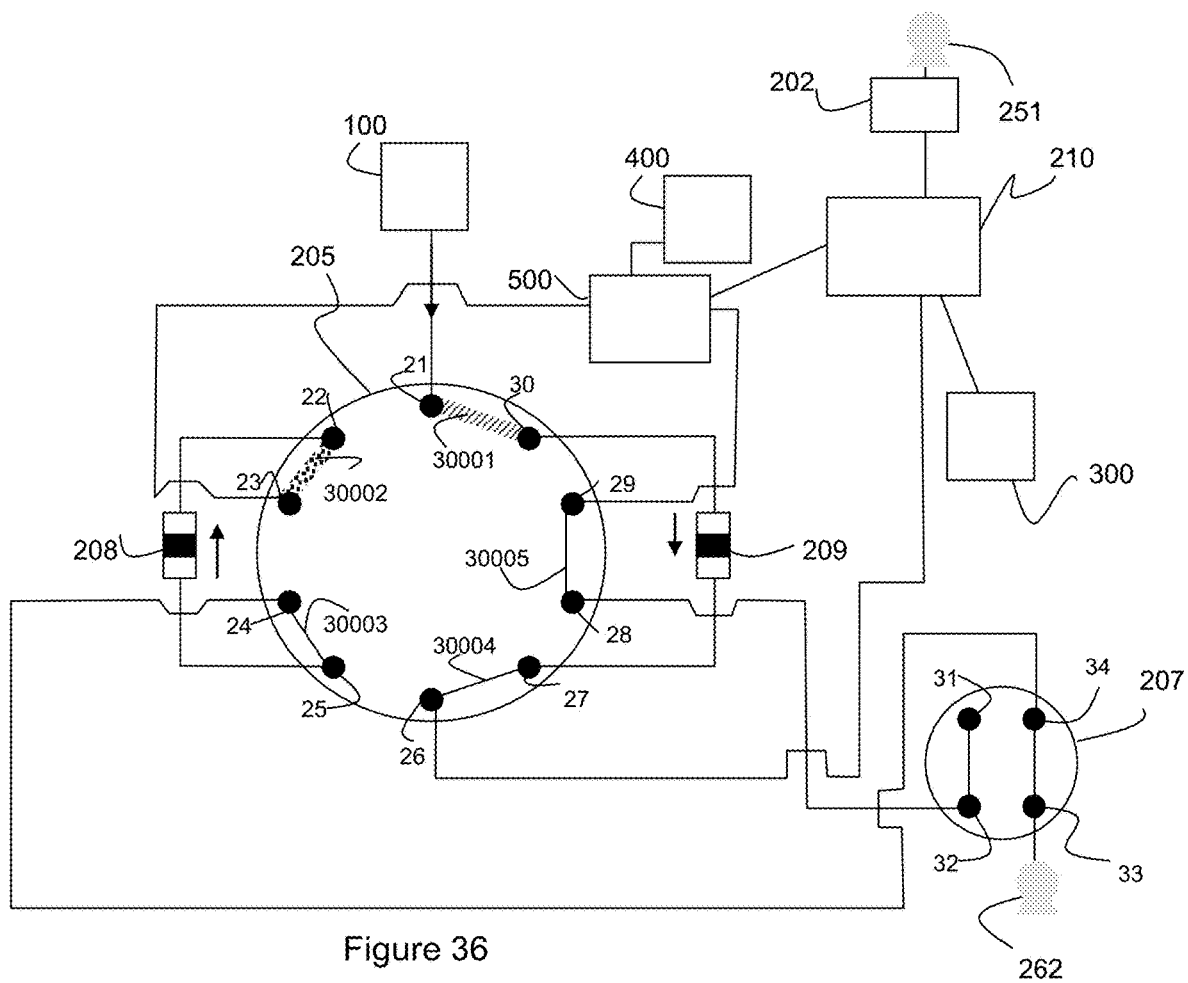
Figure 37:
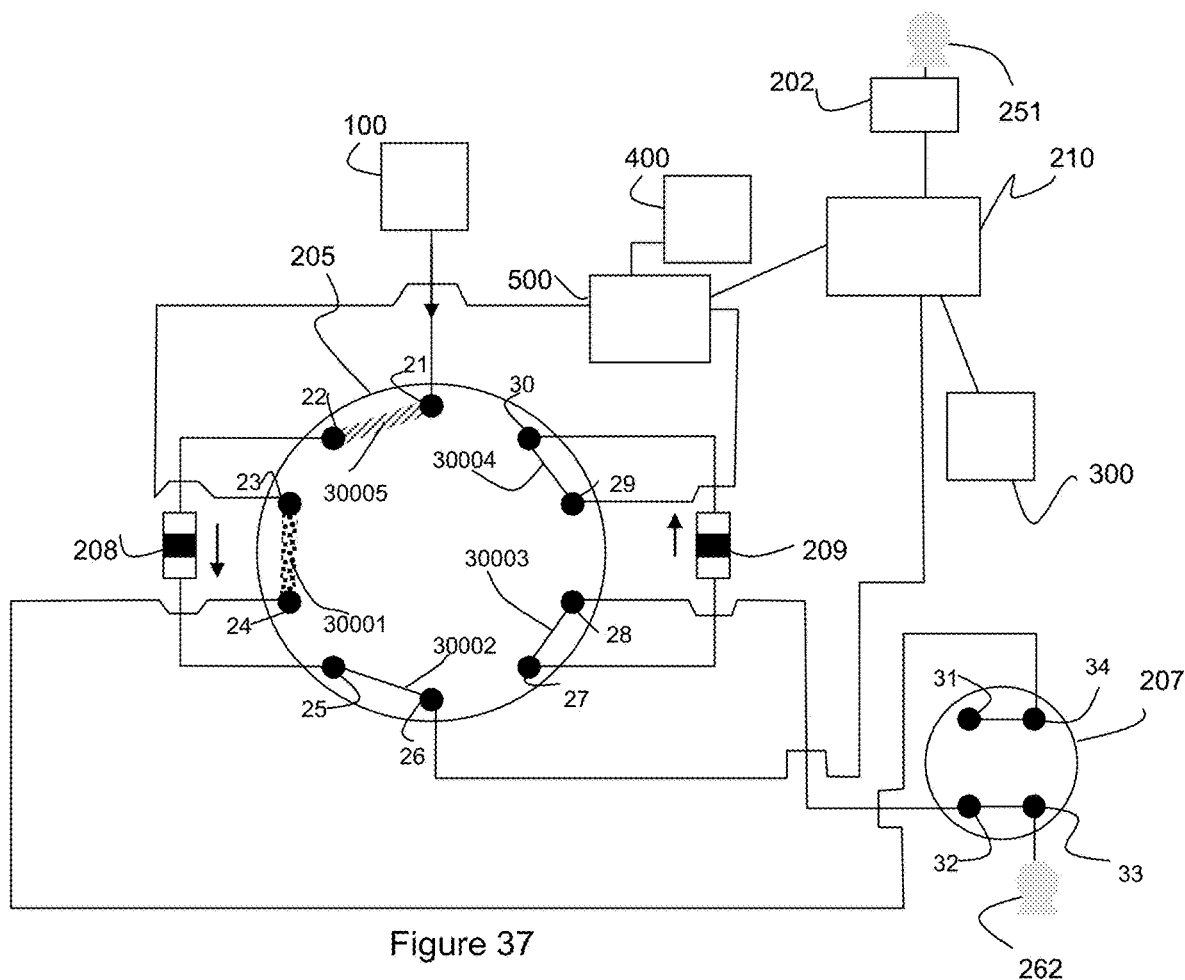
Figure 38:
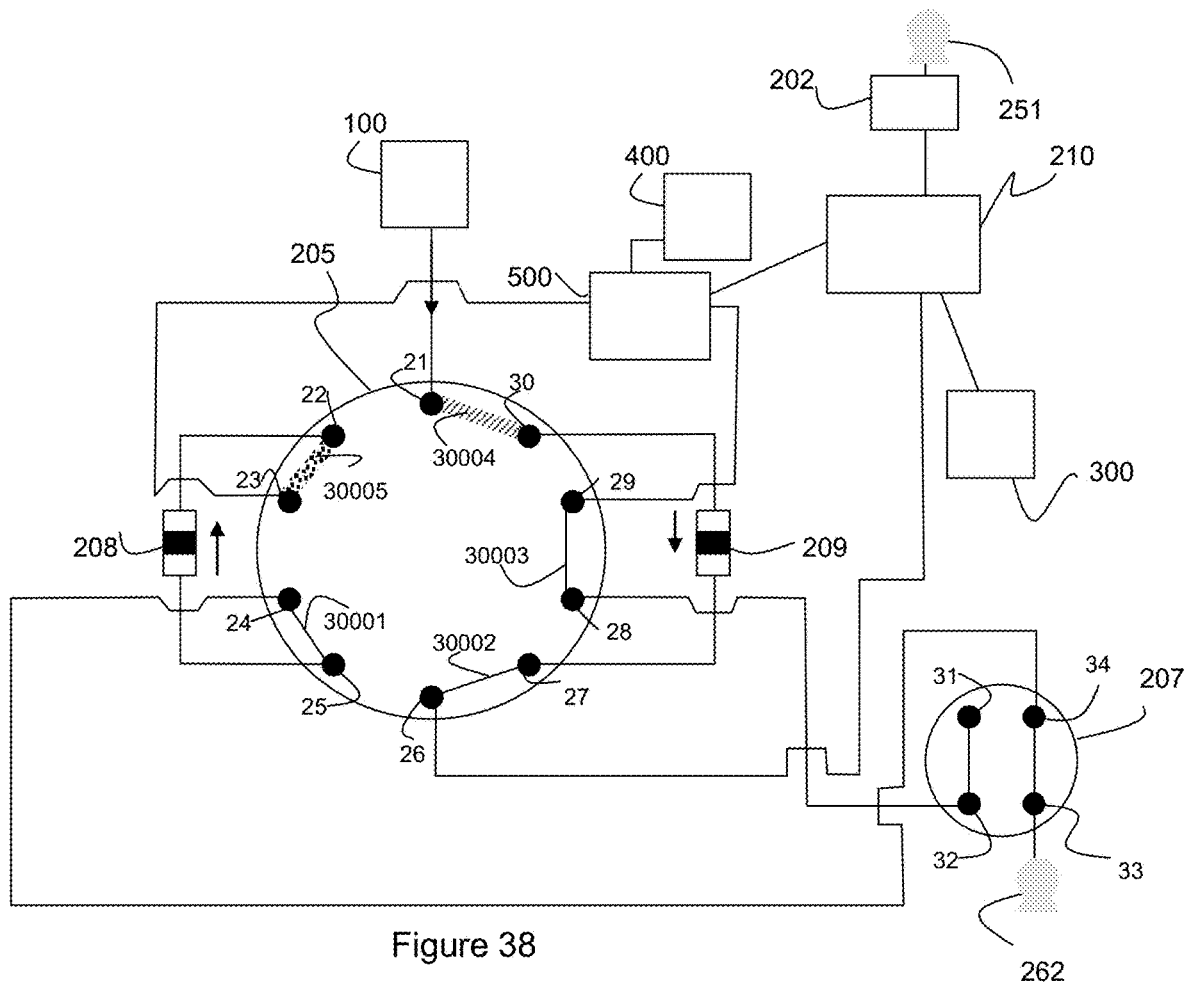
Figure 39:
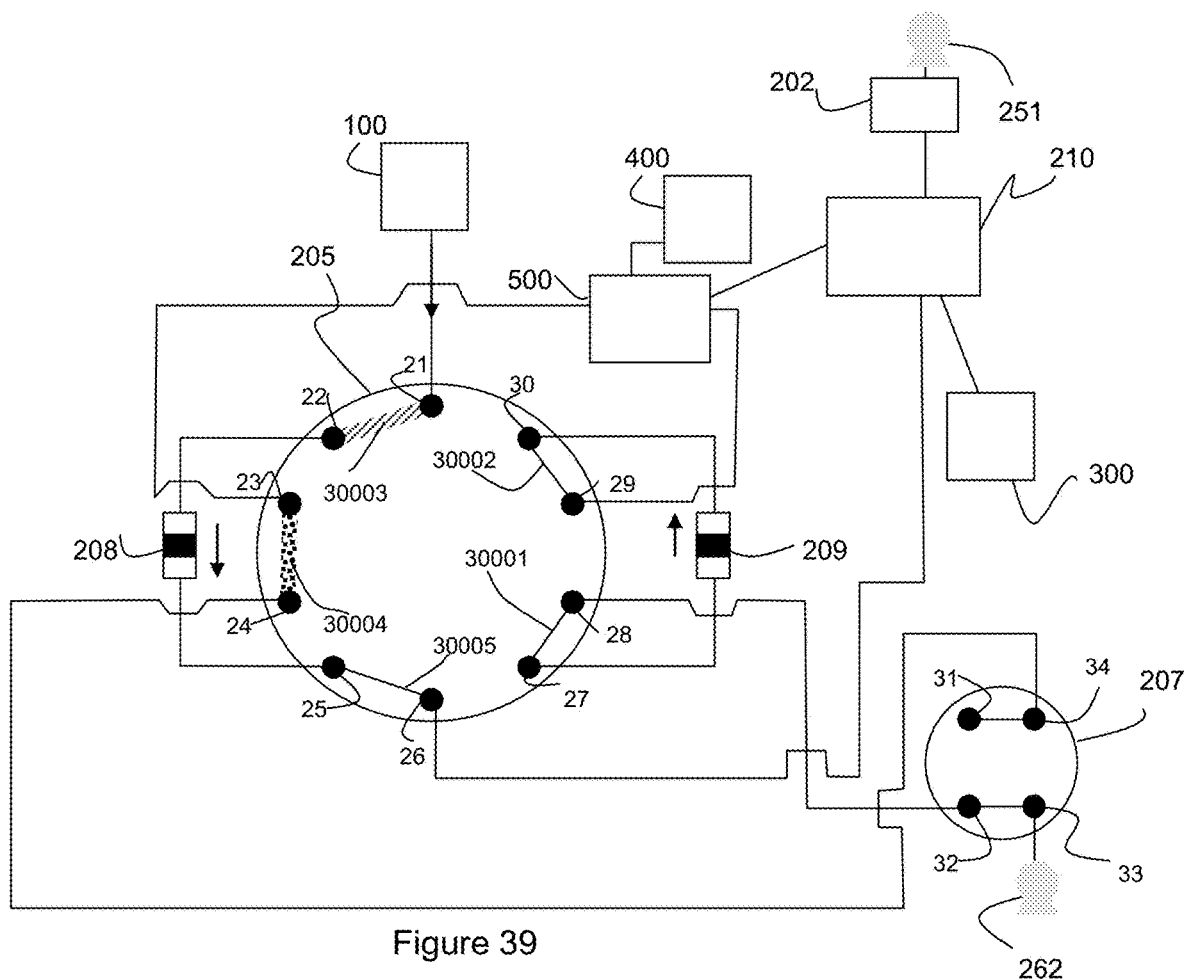

Referring to FIG. 15$_{21-22/33-32/41-46}$, in some embodiments, the filtration module is equipped with a set of multi-port valves 205 and 207.

Referring still to FIG. 15$_{21-22/33-32/41-46}$, in some embodiments, the valve 205 is a ten-port, two-position valve.

Referring still to FIG. 15$_{21-22/33-32/41-46}$, in some embodiments, the valve 207 is a four-port, two-position valve.

Referring still to FIG. 15$_{21-22/33-32/41-46}$, in some embodiments, the valve 205 is in fluid communication with a multi-port valve 210 via port 26.

Referring still to FIG. 15$_{21-22/33-32/41-46}$, in some embodiments, the valve 210 is a six-port, two-position valve.

Referring still to FIG. 15$_{21-22/33-32/41-46}$, in some embodiments, the valve 210 is in fluid communication with the valve 202 (specifically, via port 41 of the valve 210) and the sample processing module 300 (specifically, via port 43 of the valve 210).

Referring still to FIG. 15$_{21-22/33-32/41-46}$, in some embodiments, ports 42 and 45 of the valve 210 are connected by a fluid holding device 228.

Referring still to FIG. 15$_{21-22/33-32/41-46}$, in some embodiments, the valve 210 is connected to the sample delivery module 400 via port 46.

Referring still to FIG. 15$_{21-22/33-32/41-46}$, in some embodiments, valve 207 is connected via port 33 to fluid moving device 262 via port 33 of the valve 207. Port 34 of the valve 207 and port 24 of the valve 205 are connected by a fluid path 2004. Similarly, port 32 of the valve 207 and port 28 of the valve 205 are connected by a fluid path 2005.

Referring still to FIG. 15$_{21-22/33-32/41-46}$, in some embodiments, an inline filter 208 is connected between ports 22 and 25 of the valve 205. A second inline filter 209 is connected between ports 27 and 30 of the valve 205.

Referring still to FIG. 15$_{21-22/33-32/41-46}$, in some embodiments, the valve 205 is connected to the reactor module 100 via port 21.

Referring still to FIG. 15$_{21-22/33-32/41-46}$, in some embodiments, the valve 205 assumes a configuration in which specific pairs of ports (21 and 22, 23 and 24, 25 and 26, 27 and 28, 29 and 30) are in fluid communications. This configuration is referenced as $_{21-22}$.

Referring still to FIG. $15_{21-22/33-32/41-46}$, the valve 207 assumes a configuration in which specific pairs of ports (31 and 34, 32 and 33) are in fluid communications. This configuration is referenced as $_{33-32}$.

Referring still to FIG. $15_{21-22/33-32/41-46}$, the valve 210 assumes a configuration in which specific pairs of ports (41 and 46, 42 and 43, 44 and 45) are in fluid communications. This configuration is referenced as $_{41-46}$. This is a 'load' configuration of the valve 210.

Referring still to FIG. $15_{21-22/33-32/41-46}$, in some embodiments, the valve 205, 207, and 210 independently assume a combined configuration in which the valve 205 is in $_{21-22}$ configuration, the valve 207 is in $_{33-32}$ configuration and the valve 210 is in 4146 configuration. The combined configuration is labelled as $_{21-22/33-32/41-46}$ configuration. This is a 'load' configuration for the entire valve combination (205, 207, and 210).

Referring still to FIG. $15_{21-22/33-32/41-46}$, in this configuration, the reactor module 100 is in fluid communication with the sample processing module 300 via the inline filter 208 of the valve 205 and the fluid holding device 228 of the valve 210. In this configuration, fluid from the reactor module 100 is filtered in the inline filter 208 and the filtrate is moved into the fluid holding device 228. During this time, the fluid moving device 262 moves the residue through the inline filter 209 to the sample delivery module 400. The direction of flow in the inline filter 209 is opposite to the direction of flow in the inline filter 208.

Referring still to FIG. $15_{21-22/33-32/41-46}$, in some embodiments, the sample delivery module 400 is capable of diverting the residue to the sample analysis module 500. In alternate examples, the sample delivery module 400 is capable of diverting the residue to waste.

Referring still to FIG. $15_{21-22/33-32/41-46}$, in some embodiments, the port 31 of the valve 207 is not connected to any fluid path and closed.

Referring still to FIG. $15_{21-22/33-32/41-46}$, in some embodiments, the sample delivery module 400 is equipped with movable parts and is capable of receiving fluids from the fluid moving devices 251 and 262 in sequence and delivering the fluids to the sample analysis module 500 in sequence.

Referring to FIG. $16_{21-30/31-32/41-46}$, in some embodiments, the valves 205 and 207 independently assume at least a second configuration in which specific pair of ports (21 and 30, 22 and 23, 24 and 25, 26 and 27, 28 and 29, 31 and 32, 33 and 34) are connected. In this configuration, the reactor output from the reactor module 100 is first filtered through the inline filter 209 and then the filtrate is moved to the fluid holding device 228 of the valve 210. Also, in this configuration, the inline filter 208 is in fluid communication with the fluid moving device 262 and the direction of flow in the inline filter 208 is opposite to the direction of flow in the inline filter 209. This is also a 'load' configuration for the entire valve combination (205, 207, and 210).

Referring to FIG. $17_{21-30/31-32/41-42}$, in some embodiments, the valve 210 assumes at least a second configuration in which a specific pair of ports (41 and 42, 43 and 44, 45 and 46) are connected. In this configuration (inject), the fluid moving device 251 is in fluid communication with the sample delivery module 400 via the fluid holding device 228. Also, in this configuration, the filtered fluid from the valve 205, which was isolated in the fluid holding device 228, is transported to the sample analysis module 500 by the fluid moving device 251.

Referring still to FIG. $17_{21-30/31-32/41-42}$, in some embodiments, the fluid moving device 251 is in fluid communication with the fluid holding device 228 via the valve 202. In this configuration (inject), the fluid moving device 251 transports the filtered fluid in the fluid holding device 228 along with the fluidic additives from the valve 202. This is an 'inject' configuration for the entire valve combination (205, 207, and 210).

Referring to FIG. $18_{21-30/31-32/41-42/51-54}$, in some embodiments, the filtration module includes an additional multi-port valve 211.

Referring still to FIG. $18_{21-30/31-32/41-42/51-54}$, in some embodiments, the valve 211 is a four-port, two-position valve.

Referring still to FIG. $18_{21-30/31-32/41-42/51-54}$, in some embodiments, the valve 211 is in a configuration so the specific pairs of ports (51 and 54, 52 and 53) are in fluid communication. Port 23 and 24 of the valve 205 are connected to port 51 and 53 of the valve 211, respectively. The valve 207 is connected to the valve 211 via ports 34 and 52. Similarly, the sample delivery module 400 is connected to the valve 211 via port 54.

Referring still to FIG. $18_{21-30/31-32/41-42/51-54}$, in some embodiments, the fluid moving device 262 moves fluid through the inline filter 208 and the direction of flow is from port 25 to port 22.

Referring to FIG. $19_{21-30/31-32/41-42/51-52}$, in some embodiments, the valve 211 assumes at least a second configuration so the specific pairs of ports (51 and 52, 53 and 54) are in fluid communication.

Referring still to FIG. $19_{21-30/31-32/41-42/51-52}$, in some embodiments, the fluid moving device 262 moves fluid through the inline filter 208 and the direction of flow is from port 22 to port 25. In some embodiments, an additional multi-port, multi-position device is used to control the direction of flow through inline filter 209 in a similar manner.

Referring to FIG. $20_{1-2}$, when the valve 201 is a multi-position valve, the rotor of the valve 201 is moved to more than two positions.

Referring still to FIG. $20_{1-2}$, in some embodiments, the valve 201 is a ten-position valve.

Referring still to FIG. $20_{1-2}$, in some embodiments, the rotor of the valve comprises five configurable flowpaths (slits or channels), which are numbered from 10001 to 10005.

Referring still to FIG. $20_{1-2}$, in some embodiments, the configurable flowpaths are rotated so the respective flowpaths situate themselves between specific pairs of ports. For example, the configurable flowpath 10001 in the shown configuration establishes a fluid communication between the port 1 and 2. Similarly, the configurable flowpaths 10002, 10003, 10004, and 10005 establish fluid communications between the ports 3 and 4, 5 and 6, 7 and 8, 9 and 10 respectively.

Referring still to FIG. $20_{1-2}$, the reactor module 100 is in fluid communication with the sample processing module 300 via the filtration module 203 and the fluid holding device 227. This is an example of a 'load' configuration for the valve 201.

Referring still to FIG. $20_{1-2}$, in some embodiments, the sample delivery module 400 is equipped with movable parts. The sample delivery module 400 is capable of receiving fluids from the fluid moving devices 251 and 252 in sequence and delivering the fluids to the sample analysis module 500 in sequence.

Referring to FIGS. 21 to 31, in some embodiments, the valve 201 is a multi-port, multi-position valve. In these figures, the valve 201 is a ten-port and ten-position valve.

Referring to FIG. $21_{1-10}$, in some embodiments, the rotor of the valve 201 is rotated so the ports 1 and 10, 2 and 3, 4 and 5, 6 and 7, 8 and 9 are in fluid communications using the configurable flowpaths 10001, 10002, 10003, 10004, and 10005 respectively. This is an example of an 'inject' configuration.

Referring still to FIG. $21_{1-10}$, in some embodiments, the reactor module 100 is in fluid communication with the sample processing module 300 bypassing the filtration module 203 and the fluid holding device 227. In this configuration (inject), the configurable flowpath 10001 receives fluid from the reactor module 100; the configurable flowpath 10002 is in fluid communication with the fluid moving device 252 and allows fluid to move from the fluid moving device 252 to sample delivery module 400 via the filtration module 203.

Referring still to FIG. $21_{1-10}$, in some embodiments, the fluid holding device 227, which contains the filtered fluid from the reactor module 100, is in fluid communication with the fluid moving device 251 (optionally via 202) and sample delivery module 400. In this configuration the fluid moving device 251 is capable of moving the fluid from the fluid holding device 227 toward the sample delivery module 400.

Referring still to FIG. $21_{1-10}$, in some embodiments, the configurable flowpath 10002 establishes a fluid communication between the filtration module 203 and the sample delivery module 400. The fluid from the fluid moving device 252 moves through the filtration module and reaches the sample delivery module 400 in this configuration; the sample delivery module 400 moves the fluid toward the sample analysis module 500.

Referring still to FIG. $21_{1-10}$, in this configuration, the fluid moving device 252 moves fluid through the filtration module 203 and delivers the fluid to the sample delivery module 400; the sample delivery module 400 moves the fluid toward waste.

Referring still to FIG. $21_{1-10}$, in some embodiments, the sample delivery module 400 is equipped with movable parts. The delivery module 400 is capable of receiving fluids from the fluid moving devices 251 and 252 in sequence and delivering the fluids to the sample analysis module 500 in sequence.

Referring to FIG. $22_{1-2}$, in some examples, the rotor of the valve 201 is rotated to a 'load' position. In this configuration, the configurable flowpath 10001, which was previously receiving fluid from the reactor module 100, establishes a fluid communication between ports 3 and 4 (i.e., a 108° rotation counter-clockwise or 252° rotation clockwise) and the configurable flowpath 10005 receives fluid from the reactor module 100.

Referring still to FIG. $22_{1-2}$, in some embodiments, the fluid moving device 252 moves fluid toward the sample delivery module 400 via the configurable flowpath 10001. In some examples, the sample delivery module 400 moves the fluid from the fluid moving device 252 to the sample processing module 500. In alternate examples, the sample delivery module 400 moves the fluid from the fluid moving device 252 to waste.

Referring to FIG. $23_{1-10}$, in some examples, the valve 201 is in an 'inject' configuration. In this configuration, the configurable flowpath 10005, which was previously receiving fluid from the reactor module 100, moves between ports 2 and 3 (i.e., a 36° rotation counter-clockwise or 324° rotation clockwise) and the configurable flowpath 10004 receives fluid from the reactor module 100.

Referring still to FIG. $23_{1-10}$, in some embodiments, the fluid moving device 252 moves fluid toward the sample delivery module 400 via the configurable flowpath 10005. In some examples, the sample delivery module 400 moves the fluid from the fluid moving device 252 to the sample processing module 500. In alternate examples, the sample delivery module 400 moves the fluid from the fluid moving device 252 to waste.

Referring to FIG. $24_{1-2}$, in some examples, the valve 201 is in a 'load' configuration. In this configuration, the configurable flowpath 10004, which was previously receiving fluid from the reactor module 100, moves between port 3 and 4 (i.e., a 108° rotation counter-clockwise or 252° rotation clockwise) and the configurable flowpath 10003 receives fluid from the reactor module 100.

Referring still to FIG. $24_{1-2}$, in some embodiments, the fluid moving device 252 moves fluid toward the sample delivery module 400 via the configurable flowpath 10004. In some examples, the sample delivery module 400 moves the fluid from the fluid moving device 252 to the sample processing module 500. In alternate examples, the sample delivery module 400 moves the fluid from the fluid moving device 252 to waste.

Referring to FIG. $25_{1-10}$, in some examples, the valve 201 is in an "inject" configuration and the configurable flowpath 10003, which was previously receiving fluid from the reactor module 100, moves between port 2 and 3 (i.e., a 36° rotation counter-clockwise or 324° rotation clockwise) and the configurable flowpath 10002 receives fluid from the reactor module 100.

Referring still to FIG. $25_{1-10}$, in some embodiments, the fluid moving device 252 moves fluid toward the sample delivery module 400 via the configurable flowpath 10003. In some examples, the sample delivery module 400 moves the fluid from the fluid moving device 252 to the sample processing module 500. In alternate examples, the sample delivery module 400 moves the fluid from the fluid moving device 252 to waste.

Referring to FIGS. 21 to 31, in some embodiments, the valve 201 alternates between 'load' and 'inject' configurations until the valve 201 reaches to its initial configuration (FIG. $31_{1-10}$), which is same as the one in FIG. $21_{1-10}$.

Referring back to FIGS. 21 to 31, the direction of flow is controlled from the fluid moving device 252 so the movement of fluid in the configurable flowpaths is altered in either directions.

Referring to FIG. $32_{1-2/(11-12)}$, in some embodiments, the valve 204 is a multi-port, multi-position, and multi-ring valve. In this figure, the valve 204 is a twenty-port, ten-position, and two-ring valve.

Referring still to FIG. $32_{1-2/(11-12)}$, in some embodiments, the valve 204 has twenty ports distributed over two concentric rings (circles) on the stator of the valve; each circle has ten ports distributed evenly.

Referring still to FIG. $32_{1-2/(11-12)}$, in some embodiments, the rotor of the valve comprises ten configurable flowpaths (slits or channels); five configurable flowpaths are distributed evenly on the inner ring of the rotor and five remaining configurable flowpaths are distributed evenly on the outer ring of the rotor. The configurable flowpaths on the outer circle of the rotor body are numbered from 20001 to 20005.

Referring still to FIG. $32_{1-2/(11-12)}$, in some embodiments, the valve 204 is in a 'load' configuration. In this configuration, ports 1 and 2 are in a fluid communication using a configurable flowpath 20005 and receives fluid from the reactor module 100. The configurable flowpath 20001 between port 3 and 4 is in fluid communication with the fluid moving device 252.

Referring still to FIG. $32_{1-2/(11-12)}$, in some embodiments, the fluid moving device 252 moves fluid toward the sample delivery module 400 via the configurable flowpath 20001. In some examples, the sample delivery module 400 moves the fluid from the fluid moving device 252 to the sample processing module 500. In alternate examples, the sample delivery module 400 moves the fluid from the fluid moving device 252 to waste.

Referring still to FIG. $32_{1-2/(11-12)}$, in some embodiments, the sample delivery module 400 is equipped with movable parts and is capable of receiving fluids from the fluid moving devices 251 and 252 in sequence and delivering the fluids to the sample analysis module 500 in sequence.

Referring to FIG. $33_{1-10/(11-20)}$, in some examples, the valve 204 is in an 'inject' configuration and the configurable flowpath 20005, which was previously receiving fluid from the reactor module 100, moves between port 2 and 3 (i.e., a 36° rotation counter-clockwise or 324° rotation clockwise) and the configurable flowpath 20004 receives fluid from the reactor module 100.

Referring still to FIG. $33_{1-10/(11-20)}$, in some embodiments, the fluid moving device 252 moves fluid toward the sample delivery module 400 via the configurable flowpath 20005. In some examples, the sample delivery module 400 moves the fluid from the fluid moving device 252 to the sample processing module 500. In alternate examples, the sample delivery module 400 moves the fluid from the fluid moving device 252 to waste.

Referring to FIG. $34_{1-2/(11-12)}$, in some examples, the valve 204 is in a 'load' configuration and the configurable flowpath 20004, which was previously receiving fluid from the reactor module 100, moves between port 3 and 4 (i.e., a 108° rotation counter-clockwise or 252° rotation clockwise) the configurable flowpath 20003 receives fluid from the reactor module 100.

Referring to FIG. $35_{1-10/(11-20)}$, in some examples, the valve 204 is in an 'inject' configuration and the configurable flowpath 20003, which was previously receiving fluid from the reactor module 100, moves between port 2 and 3 (i.e., a 36° rotation counter-clockwise or 324° rotation clockwise) and the configurable flowpath 20002 receives fluid from the reactor module 100. The rotor of the valve 204 is rotated appropriately so the configurable flowpath, which received fluid from the reactor module 100 in the previous configuration, is in fluid communication with the fluid moving device 252 in the next configuration.

Referring back to FIGS. 32 to 35, the rotor of the valve 205 is rotated appropriately so the configurable flowpath, which was receiving fluid from the reactor module 100 in the previous configuration, is in a fluid communication with the fluid moving device 252 in the next configuration.

Referring back to FIGS. 32 to 35, the direction of flow is controlled from the fluid moving device 252 so that the movement of fluid in the configurable flowpath is altered in either directions.

Referring to FIG. $36_{21-30/31-32}$, in some embodiments, the filtration module 205 is a multi-position valve. In this figure, the filtration module 205 is a ten-position valve.

Referring still to FIG. $36_{21-30/31-32}$, in some embodiments, the rotor of the valve 205 comprises five configurable flowpaths (slits or channels), which are numbered from 30001 to 30005.

Referring still to FIG. $36_{21-30/31-32}$, in some embodiments, the rotor of the valve 205 is rotated so the respective configurable flowpaths situate themselves between specific pairs of ports. For example, the configurable flowpath 30001 in the shown configuration establishes a fluid communication between the port 21 and 30. Similarly, the configurable flowpaths 30002, 30003, 30004, and 30005 establish fluid communications between the ports 22 and 23, 24 and 25, 26 and 27, 28 and 29 respectively.

Referring still to FIG. $36_{21-30/31-32}$, in some embodiments, the configurable flowpath 30001 of the valve 205 receives fluid from the reactor module 100.

Referring still to FIG. $36_{21-30/31-32}$, the fluid moving device 262 moves fluid through the configurable flowpath 30002 in this configuration.

Referring to FIG. $37_{21-22/31-34}$, in some embodiments, the configurable flowpath 30001, which was previously receiving fluid from the reactor module 100, moves between port 23 and 24 (i.e., a 108° rotation counter-clockwise or 252° rotation clockwise) and the configurable flowpath 30005 receives fluid from the reactor module 100.

Referring to FIG. $38_{21-30/31-32}$, in some embodiments, the configurable flowpath 30005, which was previously receiving fluid from the reactor module 100, moves between port 22 and 23 (i.e., a 36° rotation counter-clockwise or 324° rotation clockwise) and the configurable flowpath 30004 receives fluid from the reactor module 100.

Referring to FIG. $39_{21-22/31-34}$, in some embodiments, the configurable flowpath 30004, which was previously receiving fluid from the reactor module 100, moves between port 23 and 24 (i.e., a 108° rotation counter-clockwise or 252° rotation clockwise) and the configurable flowpath 30003 receives fluid from the reactor module 100.

Referring back to FIGS. 36 to 39, the rotor of the valve 205 is rotated appropriately so the configurable flowpath, which was receiving fluid from the reactor module 100 in the previous configuration, is in a fluid communication with the fluid moving device 262 in the next configuration.

Referring back to FIGS. 36 to 39, the direction of flow is controlled from the fluid moving device 262 so that the movement of fluid in configurable flowpath is altered in either directions.

The invention claimed is:

1. A method for analyzing fluids comprising:
   a) configuring a fluid diverting device to receive at least a portion of a fluid stream from a reactor module to a filtration module equipped with an inline filter;
   b) flowing at least a portion of the fluid from the reactor module through the filtration module;
   c) flowing at least a portion of the fluid downstream of the inline filter to a fluid holding device;
   d) configuring the fluid diverting device to establish a fluid communication between the fluid holding device and a sample delivery module;
   e) flowing at least a portion of the fluid from the fluid holding device to the sample delivery module;
   f) flowing at least a portion of the fluid upstream of the inline filter of the filtration module to the sample delivery module;
   g) configuring the fluid diverting device to adopt more than two configurations wherein flowpaths on the configurable portion of the fluid diverting device are configured in such a manner so that any two consecutive configurations of the fluid diverting device do not have the same configurable flowpaths receiving fluid from the reactor module; and
   h) flowing at least a portion of the fluid from the sample delivery module to a sample analysis module for analysis.

2. The method of claim 1, wherein a flowpath of the configurable portion of the fluid diverting device, which was receiving fluid from the reactor module in a specific configuration, is moved to a new position so a fluid moving device can move a secondary fluid stream through the same flowpath in the next configuration.

3. The method of claim 2, wherein the secondary fluid stream is a fluid capable of removing solids from the flowpath of the configurable portion of the fluid diverting device.

4. The method of claim 1, wherein steps a), b), c), f), and g) are repeated more than one time prior to a one-time execution of step d), e), and h).

5. The method of claim 1, wherein the fluid diverting device stays in a specific configuration until the inline filter is saturated with solids.

6. The method of claim 2, wherein the configurable portion of the fluid diverting device is configured by moving the configurable portion clock-wise or counter-clockwise.

7. A method for analyzing fluids comprising:
  a) flowing at least a portion of a fluid stream from a reactor module to at least one (the first) of two inline filters (a first and a second) of a filtration module;
  b) flowing at least a portion of the fluid upstream of the second inline filter to a sample delivery module;
  c) configuring the filtration module so the fluid from the reactor module flows through the second inline filter;
  d) flowing at least a portion of the fluid upstream of the first inline filter to the sample delivery module;
  e) configuring the filtration module to adopt more than two configurations wherein flowpaths of the configurable portion of the filtration module are moved in such a manner so that any two consecutive configurations of the filtration module do not have the same configurable flowpaths receiving fluid from the reactor module;
  f) flowing the filtrate downstream from the first or the second inline filter to the sample delivery module; and
  g) flowing the filtrate from the sample delivery module to a sample analysis module for analysis.

8. The method of claim 7, wherein a flowpath of the configurable portion of the filtration module, which was receiving fluid from the reactor module in a specific configuration, is moved to a new position so a fluid moving device can move a secondary fluid stream through the same flowpath in the next configuration.

9. The method of claim 8, wherein the secondary fluid stream is a fluid capable of removing solids from the flowpaths of the configurable portion of the filtration module.

10. The method of claim 7, wherein the filtration module stays in a specific configuration until the inline filters are saturated with solids.

11. The method of claim 7, wherein the configurable portion of the filtration module is configured by moving the configurable portion clock-wise or counter-clockwise.

* * * * *